United States Patent
Kamm et al.

(10) Patent No.: US 9,993,464 B2
(45) Date of Patent: Jun. 12, 2018

(54) OTAMIXABAN FORMULATIONS WITH IMPROVED STABILITY

(71) Applicant: SANOFI, Paris (FR)

(72) Inventors: Walter Kamm, Frankfurt am Main (DE); Till Bussemer, Frankfurt am Main (DE); Doris Andert, Frankfurt am Main (DE); Bernd Kuehn, Frankfurt am Main (DE); Ernst-Josef Todt, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days. days.

(21) Appl. No.: 15/265,191

(22) Filed: Sep. 14, 2016

(65) Prior Publication Data

US 2017/0224668 A1    Aug. 10, 2017

Related U.S. Application Data

(63) Continuation of application No. 14/008,343, filed as application No. PCT/EP2012/055361 on Mar. 27, 2012, now abandoned.

(60) Provisional application No. 61/499,941, filed on Jun. 22, 2011.

(30) Foreign Application Priority Data

Mar. 29, 2011 (EP) ..................... 11305347

(51) Int. Cl.
  *A61K 31/4425* (2006.01)
  *A61K 47/12* (2006.01)
  *A61K 9/00* (2006.01)

(52) U.S. Cl.
  CPC ........ *A61K 31/4425* (2013.01); *A61K 9/0019* (2013.01); *A61K 47/12* (2013.01)

(58) Field of Classification Search
  CPC ............................ A61K 41/12; A61K 31/4425
  See application file for complete search history.

(56) References Cited

U.S. PATENT DOCUMENTS

| | | | |
|---|---|---|---|
| 3,030,272 A | 4/1962 | Schultz | |
| 6,080,767 A | 6/2000 | Klein et al. | |
| 2003/0225144 A1* | 12/2003 | Woodward | C07D 213/89 514/357 |
| 2005/0059719 A1 | 3/2005 | Badawy et al. | |
| 2014/0018398 A1 | 1/2014 | Kamm et al. | |

FOREIGN PATENT DOCUMENTS

| | | |
|---|---|---|
| EP | 0 674 510 A1 | 10/1995 |
| WO | WO-97/24118 A1 | 7/1997 |
| WO | WO-2002/028836 A1 | 4/2002 |
| WO | WO-2011/012527 A1 | 2/2011 |
| WO | WO-2012/130821 A1 | 10/2012 |

OTHER PUBLICATIONS

Waterman et al., Pharmaceutical Development and Technology, 2002;7(2):113-146.*
Cohen. M. et al., Randomized, Double-Blind, Dose-Ranging Study of Otamixaban, a Novel, Parenteral, Short-Acting Direct Factor Xa Inhibitor, in Percutaneous Coronary Intervention, *Circulation*, (2007), vol. 115, pp. 2642-2651.
Guertin, K.R. et al., The Discovery of the Factor Xa Inhibitor Otamixaban: From Lead Identification to Clinical Development, *Current Medicinal Chemistry*, (2007), vol. 14, pp. 2471-2481.
Hinder, M. et al., Anticoagulent and anti-platelet effects are maintained following coadministration of otamixaban, a direct factor Xa inhibitor, and acetylsalicyclic acid, *Thrombosis and Haemostasis*, (Jan. 1, 2006), vol. 95, pp. 224-228.
Hinder, M. et al., Direct and rapid inhibition of factor Xa by otamixaban: A pharmacokinetic and pharmacodynamics investigation in patients with coronary artery disease, *Clinical Pharmacology & Therapeutics*, (Dec. 2006), vol. 80, No. 6, pp. 691-702.
O'Neil, M. et al. (2013). "The Merck Index: An Encyclopedia of Chemicals, Drugs and Biologicals," 15th Edition, The Royal Society of Chemistry, Cambridge, UK, p. 1280.
Rebello S.S. et al., Antithrombotic efficacy of a novel factor Xa inhibitor, FXV673, in a canine model of coronary artery thrombolysis, *British Journal of pharmacology*, (2001), vol. 133, No. 7, pp. 1190-1198.
International Search Report dated Aug. 23, 2008 issued in PCT/EP2012/055361, previously submitted dated Sep. 27, 2013.

* cited by examiner

*Primary Examiner* — San Ming R Hui
(74) *Attorney, Agent, or Firm* — Morrison & Foerster LLP

(57) ABSTRACT

The invention relates to a pharmaceutical composition comprising methyl (2R.3R)-2-{3-[amino(imino)methyl]benzyl}-3-{[4-(1-oxidopyridin-4-yl)benzoyl]amino}butanoate or a pharmaceutically acceptable salt thereof and a pharmaceutically acceptable acidic reacting compound or to an aqueous solution or dispersion of the composition as well as a process for the preparation of the same, methods of using such compositions to treat subjects suffering from conditions which can be ameliorated by the administration of an inhibitor of Factor Xa.

13 Claims, No Drawings

OTAMIXABAN FORMULATIONS WITH IMPROVED STABILITY

CROSS-REFERENCE TO RELATED APPLICATIONS

This application is a continuation of U.S. patent application Ser. No. 14/008,343 (now abandoned), which adopts the international filing date of Mar. 27, 2012, which is a National Phase application under 35 U.S.C. § 371 of International Application No. PCT/EP2012/055361 filed Mar. 27, 2012, which claims priority to U.S. Provisional Application No. 61/499,941, filed Jun. 22, 2011, and claims priority benefit of EP Application No. 11305347.4, filed Mar. 29, 2011, the disclosures of each of which are incorporated herein by reference in their entirety.

FIELD OF THE INVENTION

The present invention relates to pharmaceutical compositions comprising methyl (2R,3R)-2-{3-[amino(imino)methyl]benzyl}-3-{[4-(1-oxidopyridin-4-yl)benzoyl]amino}butanoate or a pharmaceutically acceptable salt thereof, and a pharmaceutically acceptable acidic reacting compound or to an aqueous solution or dispersion of said composition, as well as a process for the preparation of the same, methods of using said compositions to treat subjects suffering from conditions which can be ameliorated by the administration of an inhibitor of Factor Xa.

BACKGROUND OF THE INVENTION

Methyl (2R,3R)-2-{3-[amino(imino)methyl]benzyl}-3-{[4-(1-oxidopyridin-4-yl)benzoyl]amino}butanoate (CAS number 193153-04-7) has the international nonproprietary name Otamixaban and shows the structure illustrated in Formula I:

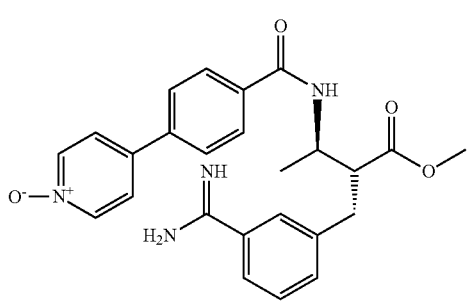

Formula I

Methyl (2R,3R)-2-{3-[amino(imino)methyl]benzyl}-3-{[4-(1-oxidopyridin-4-yl)benzoyl]amino}butanoate use in the preparation of a medicament for treating a patient suffering from, or subject to, conditions which can be ameliorated by the administration of an inhibitor of Factor Xa was disclosed in WO97/24118.

Factor Xa is the penultimate enzyme in the coagulation cascade. Factor Xa (fXa) is a critical serine protease situated at the confluence of the intrinsic and extrinsic pathways of the blood coagulation cascade. FXa catalyses the conversion of prothrombin to thrombin via the prothrombinase complex. Its singular role in thrombin generation, coupled with its potentiating effects on clot formation render it an attractive target for therapeutic intervention.

Both free factor Xa and factor Xa assembled in the prothrombinase complex (Factor Xa, Factor Va, calcium and phospholipid) are inhibited by Otamixaban. Factor Xa inhibition is obtained by direct complex formation between the inhibitor and the enzyme and is therefore independent of the plasma co-factor antithrombin III. Effective factor Xa inhibition is achieved by administering the compound either by continuous intravenous infusion, bolus intravenous administration or any other parenteral route such that it achieves the desired effect of preventing the factor Xa induced formation of thrombin from prothrombin. In vivo experiments have demonstrated that Otamixaban is highly efficacious in rodent, canine and porcine models of thrombosis. In addition, recent clinical findings indicate that Otamixaban is efficacious, safe and well tolerated in humans and therefore has considerable potential for the treatment of acute coronary syndrome (K. R. Guertin and Yong-Mi Choi; 2007; Current Medicinal Chemistry, Vol. 14, No. 23; p. 2471-2481). Clinical findings in a dose-ranging clinical trial indicate that Otamixaban reduced prothrombin fragments 1+2 significantly more than unfractionated heparin at the highest dose regimen (Cohen et al., Circulation, Vol. 115, No. 20, May 2007, pages 2642-2651), but said clinical findings do not show data in comparison of age or renal impairment. Further clinical trials demonstrated that Otamixaban induces dose-dependent, rapid direct factor Xa inhibition in patients with stable coronary artery disease who are taking their usual comedication, some of whom have mild renal impairment (Hinder et al., Clinical Pharmacology and Therapeutics, Vol. 80, No. 6, 2006, pages 691-702).

An injection and infusion pharmaceutical composition for (methyl (2R,3R)-2-{3-[amino(imino)methyl]benzyl}-3-{[4-(1-oxidopyridin-4-yl)benzoyl]amino}butanoate was developed for use in clinical studies. One of the observations made during terminal sterilization (autoclaving) and stability studies was a strong increase in two degradants. One of said degradants is (2R,3R)-2-(3-Carbamimidoyl-benzyl)-3-[4-(1-oxy-pyridin-4-yl) benzoylamino]-butyric acid and has the structure illustrated in Formula II:

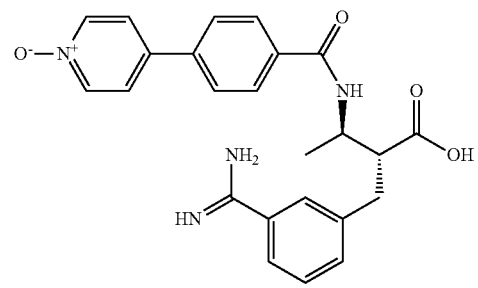

Formula II

The other of said degradants is (2R,3R)-2-(3-Carbamoyl-benzyl)-3-[4-(1-oxy-pyridin-4-yl)benzoylamino]-butyric acid methyl ester and has the structure illustrated in Formula III:

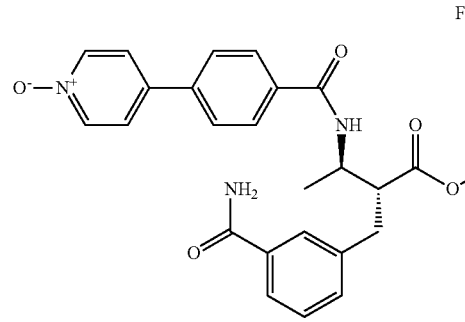

Formula III

At recommended storage conditions also elevated levels of (2R,3R)-2-(3-Carbamimidoyl-benzyl)-3-[4-(1-oxy-pyridin-4-yl)benzoylamino]-butyric acid and (2R,3R)-2-(3-Carbamoyl-benzyl)-3-[4-(1-oxy-pyridin-4-yl)benzoylamino]-butyric acid methyl ester are reached in an aqueous pharmaceutical composition containing methyl (2R,3R)-2-{3-[amino(imino)methyl]benzyl}-3-{[4-(1-oxidopyridin-4-yl)benzoyl]amino}butanoate.

It is an object of the present invention to find a long term stable pharmaceutical composition for methyl (2R,3R)-2-{3-[amino(imino)methyl]benzyl}-3-{[4-(1-oxidopyridin-4-yl)benzoyl]amino}butanoate which does not have the disadvantages of increased concentrations of (2R,3R)-2-(3-Carbamimidoyl-benzyl)-3-[4-(1-oxy-pyridin-4-yl) benzoylamino]-butyric acid or (2R,3R)-2-(3-Carbamoyl-benzyl)-3-[4-(1-oxy-pyridin-4-yl) benzoylamino]-butyric acid methyl ester which occur during terminal sterilization or long term storage.

It has been found that the formation of (2R,3R)-2-(3-Carbamimidoyl-benzyl)-3-[4-(1-oxy-pyridin-4-yl)benzoylamino]-butyric acid or (2R,3R)-2-(3-Carbamoyl-benzyl)-3-[4-(1-oxy-pyridin-4-yl)benzoylamino]-butyric acid methyl ester during long term storage of the drug product is determined by opposite effects:

During autoclaving, the levels of (2R,3R)-2-(3-Carbamoyl-benzyl)-3-[4-(1-oxy-pyridin-4-yl)benzoylamino]-butyric acid methyl ester increase significantly with increasing pH of the liquid pharmaceutical composition, whereas no strong influence of the pH of the liquid formulation on formation of (2R,3R)-2-(3-Carbamimidoyl-benzyl)-3-[4-(1-oxy-pyridin-4-yl) benzoylamino]-butyric acid was observed during autoclaving. In conclusion: The lower the pH of the pharmaceutical composition the better!

During long term storage, the levels of (2R,3R)-2-(3-Carbamimidoyl-benzyl)-3-[4-(1-oxy-pyridin-4-yl)benzoylamino]-butyric acid increase significantly with decreasing pH of the liquid pharmaceutical composition, whereas no strong influence of the pH of the liquid formulation on formation of (2R,3R)-2-(3-Carbamoyl-benzyl)-3-[4-(1-oxy-pyridin-4-yl)benzoylamino]-butyric acid methyl ester was observed during long term storage. In conclusion: The higher the pH of the pharmaceutical composition the better!

It has been found that liquid pharmaceutical compositions for methyl (2R,3R)-2-{3-[amino(imino)methyl]benzyl}-3-{[4-(1-oxidopyridin-4-yl)benzoyl]amino}butanoate or a pharmaceutically acceptable salt thereof with a pH below 5 are advantageous with respect to limiting the increase in both (2R,3R)-2-(3-Carbamimidoyl-benzyl)-3-[4-(1-oxy-pyridin-4-yl)benzoylamino]-butyric acid and (2R,3R)-2-(3-Carbamoyl-benzyl)-3-[4-(1-oxy-pyridin-4-yl)benzoylamino]-butyric acid methyl ester, influenced oppositely by autoclaving or long term storage.

A pH below 5 provides the clear advantage of the pharmaceutical compositions according to the invention which are (i) long term stable pharmaceutical compositions and (II) sterile injection solutions by autoclavation (steam sterilization), which is a simple, economic and safe method for sterilization.

SUMMARY OF THE PRESENT INVENTION

The present invention provides a pharmaceutical composition of methyl (2R,3R)-2-{3-[amino(imino)methyl]benzyl}-3-{[4-(1-oxidopyridin-4-yl)benzoyl]amino}butanoate or a pharmaceutically acceptable salt thereof, and a pharmaceutically acceptable acidic reacting compound.

The present invention provides also a sterile pharmaceutical composition of methyl (2R,3R)-2-{3-[amino(imino)methyl]benzyl}-3-{[4-(1-oxidopyridin-4-yl)benzoyl]amino}butanoate or a pharmaceutically acceptable salt thereof, and a pharmaceutically acceptable acidic reacting compound.

DETAILED DESCRIPTION OF THE INVENTION

The present invention provides a pharmaceutical composition of methyl (2R,3R)-2-{3-[amino(imino)methyl]benzyl}-3-{[4-(1-oxidopyridin-4-yl)benzoyl]amino}butanoate or a pharmaceutically acceptable salt thereof, and a pharmaceutically acceptable acidic reacting compound.

Terms used herein have the meanings defined in this specification.

"Pharmaceutically acceptable acidic reacting compound" refer to a non-toxic compound capable of imparting a pH below 5 to an aqueous solution or dispersion of methyl (2R,3R)-2-{3-[amino(imino)methyl]benzyl}-3-{[4-(1-oxidopyridin-4-yl)benzoyl]amino}butanoate or a pharmaceutically acceptable salt thereof. Illustrative acidic reacting compounds are citric acid, acetic acid, glycolic acid, adipic acid, lactic acid, pyruvic acid, malonic acid, succinic acid, glutaric acid, glucuronic acid, fumaric acid, malic acid, tartaric acid, ascorbic acid, maleic acid, hydroxymaleic acid, benzoic acid, hydroxybenzoic acid, hyaluronic acid, acetyl salicylic acid, or mineral acids such as hydrochloride acid or salts of mineral acids such as potassium dihydrogen phosphate or amino acids like glycine and its salts or a mixture of one or more of said acidic reacting compounds. Preferably, the acidic reacting compound is citric acid.

The necessary amount of a pharmaceutically acceptable acidic reacting compound for imparting a pH below 5 to an aqueous solution or dispersion of methyl (2R,3R)-2-{3-[amino(imino)methyl]benzyl}-3-{[4-(1-oxidopyridin-4-yl)benzoyl]amino}butanoate or a pharmaceutically acceptable salt thereof depends on the respective compound and can be determined by a person skilled in the art by e.g. suspending or solving a sample containing about 1 mg of methyl (2R,3R)-2-{3-[amino(imino)methyl]benzyl}-3-{[4-(1-oxidopyridin-4-yl)benzoyl]amino}butanoate in about 1 mL of purified water and adding sufficient pharmaceutically acceptable acidic reacting compound until the measured pH in the supernatant is below 5. The pH of the supernatant is measured with a pH meter or by a pH indicator.

"Buffer solution" is an aqueous solution consisting of a mixture of a weak acid and its conjugate base or a weak base and its conjugate acid. It has the property that the pH of the solution changes very little when a small amount of strong acid or base is added to it. Buffer solutions are used as a means of keeping pH at a nearly constant value in a wide variety of chemical applications.

"Degradant" refers to any drug-based materials generated after the preparation of the pharmaceutical composition according to the invention. Analysis of impurities and degradants is done using reverse phase HPLC techniques on samples as is known in the art.

"Freeze-drying" also known as "lyophilization" refers to a dehydration process.

Freeze-drying works by freezing the material and then reducing the surrounding pressure and adding enough heat to allow the frozen water in the material to sublime directly from the solid phase to the gas phase.

"i. v." refers to intravenous injection or infusion and is the giving of liquid substances directly into a vein. The word intravenous simply means "within a vein".

"Long term" refers to 1 to 3 months.

"Long term storage" refers to storage of a pharmaceutical composition for 1 to 3 months at 40° C. and 75% relative humidity.

"Very long term" refers to 3 to 6 months.

"Very long term storage" refers to storage of a pharmaceutical composition for 3 to 6 months at 40° C. and 75% relative humidity.

"mL" refers to the milliliter, defined as one-thousandth of a liter, and also often referred to by the SI derived unit name cubic centimeter.

"non-ST elevation myocardial infarction" refers to the definition of Myocardial Infarction based on ACC/AHA, ESC and WHF consensus; see also Guidelines for the diagnosis and treatment of non-ST segment elevation acute coronary syndromes; Eur Heart J, 2007, 28(13): 1598-1660.

"Normal saline" or "isotonic saline" refers to an aqueous solution of 0.9% of sodium chloride, having an osmolarity of about 308 mOsmol/L, which shows about the same osmolarity as blood plasma.

"Otamixaban" refers to the international nonproprietary name for methyl (2R,3R)-2-{3-[amino(imino)methyl]benzyl}-3-{[4-(1-oxidopyridin-4-yl)benzoyl]amino}butanoate.

"Patient" means primates such as humans or a warm blooded animal, such as for example rat, mice, dogs, cats or guinea pigs.

"Pathological condition", refers to diseases, disorders or conditions in a patient, particularly those in which Factor Xa may play a role.

"pH" is a measure of the acidity or basicity of a solution. It approximates but is not equal to p[H], the negative logarithm (base 10) of the molar concentration of dissolved hydrogen ions ($H^+$). pH determination in a solid pharmaceutical composition according to the invention is performed by suspending or dissolving a sample containing about 1 mg of Otamixaban of said pharmaceutical composition in about 1 mL of purified water. The pH of the supernatant is determined with a pH meter or by a pH indicator. pH can be measured using either pH indicators such as phenolphthaleine—in form of solution or pH strips—or using potentiometric method. Strips are very useful when 0.2 to 0.5 pH unit accuracy is requested. When a higher precision is requested, pH meter is the only way to go. In potentiometric methods the potential difference between known reference electrode and the measuring pH electrode is measured. Potential of the pH electrode depends on the activities of hydronium ions. This dependence is described by Nernst equation, thus once the potential has been measured the activity can be calculated. As a first approximation activity is identical to the ions concentration. pH meter is a device used for potentiometric pH measurements. pH meter is nothing else but precise voltmeter, connected to the pH electrode, and scaled in such a way that it displays not the measured potential, but already the pH value.

"Pharmaceutically acceptable salt" is any acid salt of the base compound methyl (2R,3R)-2-{3-[amino(imino)methyl]benzyl}-3-{[4-(1-oxidopyridin-4-yl)benzoyl]amino}butanoate which is able to be administered in pharmaceutical compositions for preclinical and clinical use. Illustrative inorganic acids which form suitable salts include mineral acids, such as hydrochloric acid, phosphoric acid and sulfamic acid; and organic acids such as acetic acid, citric acid, lactic acid, tartaric acid, malonic acid, benzoate, amino acids and the like. Preferably, the acid addition salt is derived from a mineral acid, with hydrochloric acid being preferred.

"RH" refers to relative humidity; the relative humidity of an air-water mixture is defined as the ratio of the partial pressure of water vapor in the mixture to the saturated vapor pressure of water at a prescribed temperature.

"Sterilization" refers to any process that effectively kills or eliminates transmissible agents such as fungi, bacteria, viruses or spore forms from the pharmaceutical composition. Sterilization can be achieved e.g. through application of heat, chemicals, irradiation, high pressure or filtration or a combination thereof.

"Steam sterilization" refers to a widely-used method for heat sterilization in an autoclave. Autoclaves commonly use steam heated to 121° C. to 134° C. To achieve sterility, an effective holding time of at least 15 minutes at 121° C. or 3 minutes at 134° C. is required. Proper autoclave treatment will inactivate all fungi, bacteria, viruses and also bacterial spores, which can be quite resistant.

"Sterilization through filtration" refers to a method generally used for liquids that would be damaged by heat, irradiation or chemical sterilization. A filter with pore size 0.2 μm will effectively remove bacteria. If viruses must also be removed, a much smaller pore size around 20 nm is needed.

"Therapeutically effective amount" means an amount of the compound, which is effective in treating the named disorder or condition.

"Tonicity" means a measure of the osmotic pressure (as defined by the water potential of the two solutions) of two solutions which are separated by a semi permeable membrane. It is commonly used when describing the response of living cells immersed in an external solution. Like osmotic pressure, tonicity is influenced only by the solutes that cannot cross the membrane, as only these exert an osmotic pressure. Solutes able to freely cross the membrane do not affect tonicity because they will after some time be in equal concentrations on both sides of the membrane.

"Treat" or "treating" means any treatment, including, but not limited to, alleviating symptoms, eliminating the causation of the symptoms either on a temporary or permanent basis, or preventing or slowing the appearance of symptoms and progression of the named disorder or condition.

The synthesis of methyl (2R,3R)-2-{3-[amino(imino)methyl]benzyl}-3-{[4-(1-oxidopyridin-4-yl)benzoyl]amino}butanoate has been disclosed, and is accomplished by methods that are well known to those skilled in the art. For example International Application WO97/24118 discloses methods of synthesis.

Examples of acidic reacting compounds are organic acids such as citric acid, acetic acid, glycolic acid, lactic acid, pyruvic acid, malonic acid, succinic acid, glutaric acid, fumaric acid, malic acid, tartaric acid, ascorbic acid, maleic acid, hydroxymaleic acid, benzoic acid, hydroxybenzoic acid, phenylacetic acid, hyaluronic acid, acetyl salicylic acid, cinnamic acid, salicyclic acid, 2-phenoxybenzoic acid, p-toluenesulfonic acid and sulfonic acids such as methanesulfonic acid and 2-hydroxyethanesulfonic acid or its salts or a mixture of one or more of said organic acids and its salts. Further examples of acidic reacting compounds are mineral acids such as hydrochloride acid or phosphoric acid or salts of mineral acids such as potassium dihydrogen phosphate, or amino acids and its salts or a mixture of one or more of said mineral acids or amino acids and its salts. Preferably, the acidic reacting compound is citric acid or sodium citrate or a mixture thereof.

In a further embodiment of the invention the addition of an acidic reacting compound to Otamixaban creates a pH from about pH 3 to about pH 4.5, or from about pH 3.7 to about pH 4.3, about pH 3.8 to about pH 4.3, or from about pH 4.0 to about pH 4.2 or of about pH 4.0 in the pharmaceutical composition according to the invention. The pH determination is performed after taken a sample from said pharmaceutical composition. The pH is determined with a pH meter or by a pH indicator.

In a further embodiment the invention relates to an aqueous pharmaceutical composition for injection containing
a) from 0.1 mg/mL to 60 mg/mL (2R,3R)-2-{3-[amino(imino)methyl]benzyl}-3-{[4-(1-oxidopyridin-4-yl)benzoyl]amino}butanoate, or from 1.5 mg/mL to 50 mg/mL or from 5 mg/mL to 25 mg/mL,
b) from 1 mMol/L to 1000 mMol/L acidic reacting compound or its salt or a mixture thereof, or from 20 mMol to 25 mMol, or from 4 mMol to 6 mMol, and
c) possesses a pH below 5.0.

In a further embodiment the invention relates to an aqueous pharmaceutical composition containing from 0.8 mg/mL to 30 mg/mL (2R,3R)-2-{3-[amino(imino) methyl]benzyl}-3-{[4-(1-oxidopyridin-4-yl)benzoyl]amino}butanoate, or from 0.9 mg/mL to 26 mg/mL, or from 0.9 mg/mL to 6 mg/mL. In a further embodiment the invention relates to an aqueous pharmaceutical composition containing from 2.0 mg/mL to 30 mg/mL (2R,3R)-2-{3-[amino(imino)methyl]benzyl}-3-{[4-(1-oxidopyridin-4-yl)benzoyl]amino}butanoate, or from 2.0 mg/mL to 25 mg/mL, or from 16 mg/mL to 25 mg/mL or from 3.0 mg/mL to 6 mg/mL.

In a further embodiment the invention relates to an aqueous pharmaceutical composition wherein a buffer solution is used as an acidic reacting compound which is capable of imparting a pH below 5.0 to an aqueous solution or dispersion of the composition of methyl (2R,3R)-2-{3-[amino(imino)methyl]benzyl}-3-{[4-(1-oxidopyridin-4-yl)benzoyl]amino}butanoate or a pharmaceutically acceptable salt thereof. In this further embodiment the addition of a buffer solution to Otamixaban creates a pH from about pH 3 to about pH 5.0, or from about pH 3 to about pH 4.7, or from about pH 3.5 to about pH 4.6 or from about pH 3.6 to about pH 4.3, from about pH 3.6 to about pH 4.2, or from about pH 3.6 to about pH 4.1 in the aqueous pharmaceutical composition.

Illustrative examples of suitable buffers contain buffering substances such as citric acid and its sodium or potassium salt, phosphoric acid and its sodium or potassium salt or hydrogen phosphate, or dibasic sodium phosphate, acetic acid and its sodium salt, lactic acid and its salts, succinic acid and its salts, tartaric acid and its salts, ascorbic acid and its salts, aspartic acid and its salts, benzoic acid and its salts, adipic acid and its salts, glucuronic acid and its salts, or mineral acids such as hydrochloride acid or salts, amino acids and its salts like glycine or serine or mixtures of such buffering substances. Preferred examples are mixtures of citric acid and sodium citrate. Examples of such mixtures are citric acid with sodium citrate (monosodium citrate, disodium citrate) and citric acid or potassium dihydrogen phosphate and hydrogen phosphate.

In a further embodiment of the invention the concentration of the buffer solution which creates a pH below 5.0 in an aqueous pharmaceutical composition is from 1 mMol/L to 1000 mMol/L or from 20 mMol to 25 mMol, or from 4 mMol to 6 mMol.

In a further embodiment of the invention additional tonicity adjuster could be added to the liquid pharmaceutical preparation according to the invention to receive a solution showing an osmolarity from 260 mOsmol/L to 350 mOsmol/L or of about 308 mOsmol/L, which has about the same or similar osmolarity as blood plasma.

Illustrative examples for tonicity adjuster are salts such as sodium chloride or sugars like glucose or sugar alcohols like mannitol. In case of sterilization by autoclaving salts or sugar alcohols such as mannitol are preferred. The concentration for salts can be from 0 mg/mL to 20 mg/mL, dependent on the concentration of Otamixaban and of the acidic reacting compound. The concentration for glucose or sugar alcohols like mannitol can be from 0 mg/mL to about 60 mg/mL, dependent on the concentration of Otamixaban and of the acidic reacting compound. The tonicity of the whole solution shall not exceed and osmolarity from 260 mOsmol/L to 350 mOsmol/L.

Aqueous pharmaceutical compositions according to the invention may be prepared by incorporating methyl (2R,3R)-2-{3-[amino(imino)methyl]benzyl}-3-{[4-(1-oxidopyridin-4-yl)benzoyl]amino}butanoate or a pharmaceutically acceptable salt thereof, and an acidic reacting compound in the respective required amounts, in water with various of the other ingredients enumerated herein, as required, followed by mixture for an appropriate time.

In a further embodiment the invention relates to a sterile pharmaceutical composition of methyl (2R,3R)-2-{3-[amino(imino)methyl]benzyl}-3-{[4-(1-oxidopyridin-4-yl)benzoyl]amino}butanoate or a pharmaceutically acceptable salt thereof, and a pharmaceutically acceptable acidic reacting compound in an aqueous solution or a dispersion of the composition.

In a further embodiment the invention relates to a sterile aqueous pharmaceutical composition of methyl (2R,3R)-2-{3-[amino(imino)methyl]benzyl}-3-{[4-(1-oxidopyridin-4-yl)benzoyl]amino}butanoate or a pharmaceutically acceptable salt thereof, a pharmaceutically acceptable acidic reacting compound and water at a pH below 5.0 or a dispersion of the composition.

Sterile pharmaceutical composition can be prepared by sterilization the pharmaceutical composition according to the invention. Sterilization refers to any process that effectively kills or eliminates transmissible agents such as fungi, bacteria, viruses or spore forms from the pharmaceutical composition. Sterilization can be achieved through application of heat, chemicals, irradiation, high pressure or filtration. Steam sterilization is a preferred method of sterilization and refers to method for heat sterilization in an autoclave. Autoclaves commonly use steam heated to 121° C. to 134° C. To achieve sterility, a holding time of at least 15 minutes at 121° C. or 3 minutes at 134° C. is required. Additional sterilizing time may be required for liquids and instruments if the vials with the solution or powder are additionally packed in layers of cloth, as they may take longer to reach the required temperature.

Sterile liquid pharmaceutical composition according to the invention may be prepared by incorporating methyl (2R,3R)-2-{3-[amino(imino)methyl]benzyl}-3-{[4-(1-oxidopyridin-4-yl)benzoyl]amino}butanoate or a pharmaceutically acceptable salt thereof and a pharmaceutically acceptable acidic reacting compound, in the required amounts, in water, and optionally with various of the other ingredients enumerated herein, as required, followed by sterilization. Sterilization can be achieved through application of heat, chemicals, irradiation, high pressure or filtration.

Generally, dispersions may be prepared by incorporating the sterilized methyl (2R,3R)-2-{3-[amino(imino)methyl]benzyl}-3-{[4-(1-oxidopyridin-4-yl)benzoyl]amino}butanoate or a pharmaceutically acceptable salt thereof and a pharmaceutically acceptable acidic reacting compound into a sterile vehicle which contains the dispersion medium and the other ingredients enumerated herein.

Powders for injections or infusions are solid, sterile substances or mixtures of substances including methyl (2R,3R)-2-{3-[amino(imino)methyl]benzyl}-3-{[4-(1-oxidopyridin-4-yl)benzoyl]amino}butanoate and a pharmaceutically acceptable acidic reacting compound, distributed in their final containers and which, when shaken with the prescribed volume of a prescribed sterile liquid rapidly form clear and practically particle-free solutions. After dissolution, they comply with the requirements for injections or for infusions. The mixing of the substances can be carried out using any of the mixing techniques known in the art.

Freeze-dried products for parenteral use are considered as powders for injections or infusions.

In providing Otamixaban and pharmaceutically acceptable acidic reacting compound compositions in solid forms, the Otamixaban and a pharmaceutically acceptable acidic reacting compound and optionally further components of the pharmaceutical composition according to the invention can be mixed as powders. This mixing can be carried out using any of the mixing techniques known in the art. The mixing is preferably carried out using a high shear mixer, V-blender (or other twin-shell blender), bin blender or Turbula mixer-shaker. Blending is typically carried out for sufficient time to assure complete mixing. Once the blend is made the solid form is prepared by procedures known in the art.

In the case of sterile powders for the preparation of sterile pharmaceutical compositions, the preferred methods of preparation may include vacuum drying and the freeze drying technique which may yield a powder of the methyl (2R,3R)-2-{3-[amino(imino)methyl]benzyl}-3-{[4-(1-oxidopyridin-4-yl)benzoyl]amino}butanoate or a pharmaceutically acceptable salt thereof, and a pharmaceutically acceptable acidic reacting compound and optionally plus any additional ingredients enumerated herein such as from the previously sterile-filtered solution or steam sterilized solution thereof. Sterilization of the prepared powder can be achieved through application of heat, chemicals or irradiation. Steam sterilization is a preferred method of sterilization and refers to method for heat sterilization in an autoclave. The powder is sterilized in an appropriate vial or vehicle.

The sterile powder can be stored until a sterile injectable solution is prepared by adding a pre-sterilized appropriate solvent such as water followed by mixing of the composition. It is also possible to add a pre-sterilized appropriate solvent and store the prepared liquid pharmaceutical composition.

In a further embodiment the invention relates to an aqueous pharmaceutical composition for injection containing a maximum impurity level of (2R,3R)-2-(3-Carbamimidoyl-benzyl)-3-[4-(1-oxy-pyridin-4-yl)benzoylamino]-butyric acid that does not exceed about 8.0% after long term storage. In some embodiments, the maximum impurity level of (2R,3R)-2-(3-Carbamimidoyl-benzyl)-3-[4-(1-oxy-pyridin-4-yl) benzoylamino]-butyric acid is from 0.3% to 4.0%, or from 0.4% to 3.0%, or from 0.4% to 1.8%, or from 0.4% to 0.8%, or from 0.43% to 0.7%.

In a further embodiment the invention relates to an aqueous pharmaceutical composition for injection containing a maximum impurity level of (2R,3R)-2-(3-Carbamoyl-benzyl)-3-[4-(1-oxy-pyridin-4-yl)benzoylamino]-butyric acid methyl ester that does not exceed about 5.0% after long term storage. In some embodiments, the maximum impurity level of (2R,3R)-2-(3-Carbamoyl-benzyl)-3-[4-(1-oxy-pyridin-4-yl)benzoylamino]-butyric acid methyl ester is from 0.7% to 4.5%, or from 0.8% to 4.0%, or from 0.9% to 3.5%, or from 1.2% to 2.2%, or from 1.4% to 2.0%.

In a further embodiment the invention relates to an aqueous pharmaceutical composition for injection containing a maximum total impurity level that does not exceed about 13%. In some embodiments, the total impurity level is from 1.0% to 8.5%, or from 1.1% to 8.0%, or from 1.3% to 6.0%, or from 1.6% to 4.0%, or from 1.8% to 3.5%.

The relative amounts of methyl (2R,3R)-2-{3-[amino(imino)methyl]benzyl}-3-{[4-(1-oxidopyridin-4-yl)benzoyl]amino}butanoate and acid counterion in its salts may vary and depends, for example, on the particular acid selected and the methods employed in preparing the salts. Preferably, the salts of the present invention comprise about one equivalent of acid for about each equivalent of methyl (2R,3R)-2-{3-[amino(imino)methyl]benzyl}-3-{[4-(1-oxidopyridin-4-yl)benzoyl]amino}butanoate.

The acid addition salts of (methyl (2R,3R)-2-{3-[amino(imino)methyl]benzyl}-3-{[4-(1-oxidopyridin-4-yl)benzoyl]amino}butanoate may be prepared by dissolving the free base in aqueous or aqueous-alcohol solution or other suitable solvents containing the appropriate acid or to which the appropriate acid is added, and isolating the salt by evaporating the solution, or by reacting the free base and acid in an organic solvent, in which case the salt may separate directly and/or may be obtained by concentration of the solution.

The pharmaceutical compositions of the present invention may be useful in inhibiting Factor Xa. Accordingly, the present invention provides methods for the treatment or prevention of a pathological condition that may be capable of being modulated by inhibiting production of Factor Xa.

Examples of pathological conditions that may be capable of being treated with the pharmaceutical compositions of the present invention include, for example, acute myocardial infarction (AMI), non-ST elevation myocardial infarction, unstable angina, thromboembolism, acute vessel closure associated with thrombolytic therapy, percutaneous transluminal coronary angioplasty (PTCA), transient ischemic attacks, stroke, intermittent claudication, and restenosis.

The pharmaceutical compositions described herein thus may be useful for, inter alia, inhibiting blood coagulation by virtue of their general ability to inhibit the penultimate enzyme in the coagulation cascade, Factor Xa, rather than thrombin. Pharmaceutical compositions within the scope of the present invention may exhibit marked pharmacological activities according to tests described in the literature, including in vivo tests and in vitro tests, the latter of which are believed to correlate to pharmacological activity in humans and other mammals. For example, both free Factor Xa and Factor Xa assembled in the prothrombinase complex (Factor Xa, Factor Va, calcium and phospholipid) may be inhibited. Factor Xa inhibition may be obtained by direct complex formation between the inhibitor and the enzyme and is therefore independent of the plasma co-factor antithrombin III. Effective Factor Xa inhibition may be achieved by administering the pharmaceutical composition according to the invention by continuous intravenous infusion, bolus intravenous administration or any other suitable route such that it may achieve the desired effect of preventing the Factor Xa induced formation of thrombin from prothrombin.

In addition to their use in anticoagulant therapy, Factor Xa inhibitors may be useful in the treatment or prevention of other diseases in which the generation of thrombin may play a pathologic role. For example, thrombin has been proposed to contribute to the morbidity and mortality of such chronic and degenerative diseases as arthritis, cancer, atherosclerosis and Alzheimer's disease by virtue of its ability to regulate many different cell types through specific cleavage and activation of a cell surface thrombin receptor.

Inhibition of Factor Xa may effectively block thrombin generation and therefore neutralize any pathologic effects of thrombin on various cell types.

Methods of delivering the injectable aqueous pharmaceutical composition parenterally are well known in the art. For example, the injectable aqueous pharmaceutical composition may be delivered intravenously in a specific dosage form. Said dosage form may be delivered in an intravenous infusion dose.

In general in the adult population, suitable infusion doses of methyl (2R,3R)-2-{3-[amino(imino)methyl]benzyl}-3-{[4-(1-oxidopyridin-4-yl)benzoyl]amino}butanoate may range from 0.07 mg/Kg body weight/h to 0.14 mg/Kg body weight/h. Further suitable doses may range from 0.08 mg/Kg body weight/h to 0.12 mg/Kg body weight/h. Said dosage form may also be delivered in an intravenous bolus dose. In general in the adult population, suitable infusion doses of methyl (2R,3R)-2-{3-[amino(imino)methyl]benzyl}-3-{[4-(1-oxidopyridin-4-yl)benzoyl]amino}butanoate may range from 0.07 mg/Kg body weight to 0.14 mg/Kg body weight. Also a suitable dose balancing patient safety and efficacy will be a dose close to 0.1 mg/kg body weight/h after i.v. bolus of approximately 0.08 mg/kg body weight.

Said injectable dosage form may be administrated with other drug products such as glycoprotein IIb/IIa inhibitors, unfractionated heparin, low molecular weight heparins, enoxaparin, or clopidogrel. Alternatively, said injectable dosage form may be combined with blood thinners including, but not limited to, coumadin, warfarin, or aspirin.

Liquid injectable pharmaceutical compositions according to the invention may be prepared by incorporating methyl (2R,3R)-2-{3-[amino(imino)methyl]benzyl}-3-{[4-(1-oxidopyridin-4-yl)benzoyl]amino}butanoate or a pharmaceutically acceptable salt thereof and an acidic reacting compound or buffer in the required amounts, in water, with optionally various of the other ingredients enumerated herein, as required, followed by mixing for an appropriate time.

Liquid pharmaceutical compositions may also contain other components routinely utilized in formulating pharmaceutical compositions. One example of such components is lecithin. Its use in compositions of the invention as an emulsifying agent may range from about 0.05 to about 1% by weight, and all combinations and subcombinations of ranges and specific amounts therein. More preferably, emulsifying agents may be employed in an amount of from about 0.1 to about 0.5% by weight. Other examples of components that may be used are antimicrobial preservatives, such as benzoic acid or parabens; suspending agents, such as Polysorbate 80. The selection of such optional components and their level of use in the compositions of the invention is within the level of skill in the art and will be even better appreciated from the working examples provided hereinafter.

In general, water, a suitable oil, saline, and glycols, such as propylene glycol or polyethylene glycols may be suitable solvents for liquid pharmaceutical compositions. Suitable solutions for liquid pharmaceutical compositions may be prepared by dissolving methyl (2R,3R)-2-{3-[amino(imino)methyl]benzyl}-3-{[4-(1-oxidopyridin-4-yl)benzoyl]amino}butanoate or a pharmaceutically acceptable salt thereof and an acidic reacting compound in the solvent and, if necessary, adding buffering substances. Anti-oxidizing agents, such as sodium bisulfite, sodium sulfite, or ascorbic acid either alone or combined, may be additionally added. Sodium EDTA may also be employed.

Useful pharmaceutical dosage-forms for administration methyl (2R,3R)-2-{3-[amino(imino)methyl]benzyl}-3-{[4-(1-oxidopyridin-4-yl)benzoyl]amino}butanoate or a pharmaceutically acceptable salt thereof can be illustrated as follows:

Injectable

A parenteral composition suitable for administration by injection may be prepared by stirring from 1 mg to 30 mg/mL by weight of methyl (2R,3R)-2-{3-[amino(imino)methyl]benzyl}-3-{[4-(1-oxidopyridin-4-yl)benzoyl] amino}butanoate, or a pharmaceutically acceptable salt thereof, in 1 mL to 200 mL of water and adding under mixing from 2 mg/mL to 4 mg/mL by weight of sodium citrate and from 2 mg/mL to 4 mg/mL of citric acid monohydrate and 5 mg/mL to 8 mg/mL sodium chloride. Finally the pH is adjusted to pH 4 by the addition of sodium hydroxide or hydrochloric acid. The prepared solution is filtered and filled in an appropriate vial. The solution and the vial are sterilized by steam sterilization in an autoclave. Autoclaves commonly use steam heated to 121° C. to 134° C. To achieve sterility, a holding time of at least 15 minutes can be used.

The following non-limiting examples illustrate the inventors' preferred methods for preparing and using the pharmaceutical compositions of the present invention.

EXAMPLES

Example 1—Preparation of Compound (V)

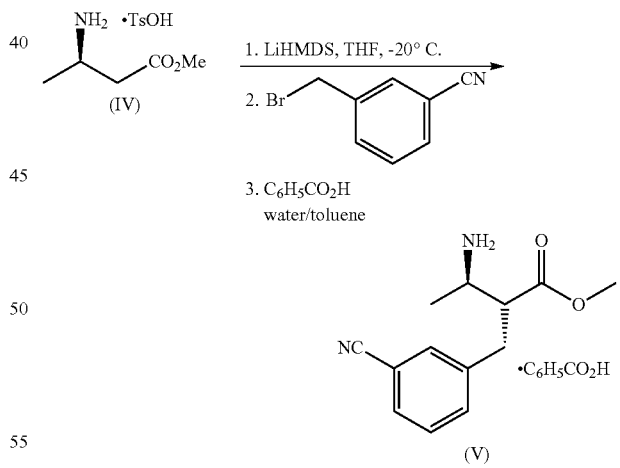

TsOH is p-Toluenesulfonic acid with the formula $CH_3C_6H_4SO_3H$. TsOH refers to the monohydrate. To a reactor were charged Compound (IV) (100.0 g) and anhydrous tetrahydrofuran (THF) (320 g). The resulting suspension was cooled down to −20±3° C. and lithium hexamethyldisilazide (LiHMDS) (475.6 grams, 1.3 M solution in THF) was added over 55 minutes and stirred for 20 minutes at −20±3° C. A solution of α-bromo-m-tolunitrile in THF (65.1 g in 181 g of THF) was then charged into the reactor over 40 minutes while maintaining the temperature at −20±3° C. and stirred for another 30 minutes. Benzoic acid (126.6 grams) was charged as a solid to the reactor. Water (1000 g) was then added and mixture distilled at a 65±3° C. jacket temperature and 200-233 mbar vacuum. After distilling to a constant pot temperature of 57° C. and constant head temperature of 45° C., the distillation was stopped. Toluene (432 g) was added to the hot solution and stirred while cooling down to 10±2° C. The resulting suspension was then filtered and the filter cake washed with water (250 grams) and toluene (432 grams). Compound (V) was dried at 45-50° C. at 350 mbar vacuum under a nitrogen stream for 24 hours until constant weight. The isolated solid weighed 76.0 grams (62.0% yield).

Example 2—Preparation of Compound (VII)

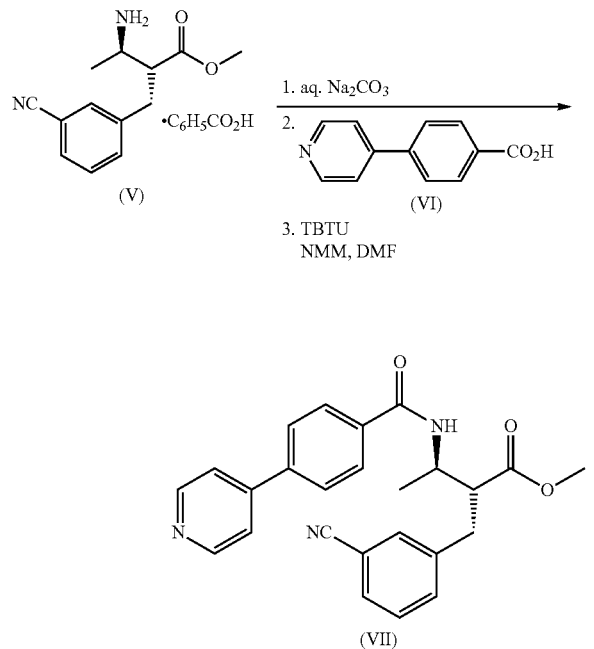

Compound (V) was partitioned between dichloromethane and aqueous sodium carbonate. The organic phase (containing the free base of (V)) was washed with additional aqueous sodium carbonate and was distilled under reduced pressure and solvent exchanged with dimethylformamide (DMF). This solution was assayed for wt/wt content of (V). To a suspension of (VI) (1.0 equivalent vs. (V)) in DMF were added 2 equivalents of 4-methylmorpholine and 1.1 equivalents of O-Benztriazol-1-yl-N,N,N',N'-tetramethyluronium tetrafluoroborate (TBTU). This mixture was stirred at ambient temperature until ester activation was complete (about 90 minutes). The DMF solution of Compound (V) (1 equivalent) was added and the resulting solution stirred overnight after which HPLC indicated that the reaction was complete. Water was added at 75° C. and the mixture was cooled to crystallize the product. The mixture was cooled to 5° C., filtered, and the filter cake was washed with water. The product was dried under reduced pressure at 70° C.

Example 3—Preparation of Compound (VIII)

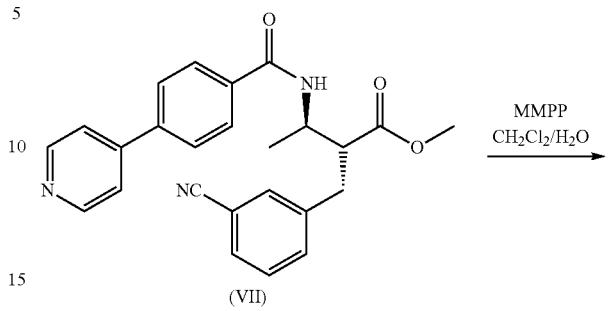

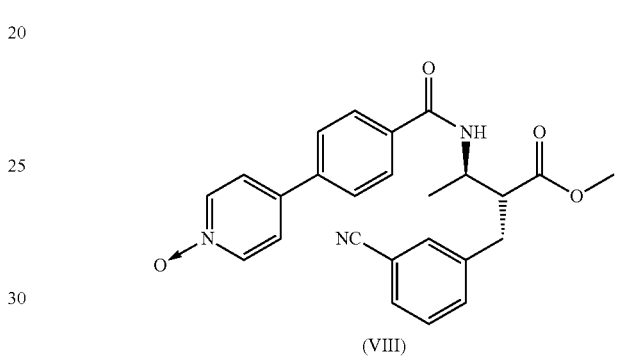

In a well-stirred reactor, 45 g of compound (VII) in 450 mL dichloromethane was reacted for at least 5 hours with 61 g of magnesium monoperoxyphthalate (66.4% based on available oxygen, 1.5 eq.) in 450 g of water until the reaction was complete. The phases were separated and the organic phase was washed successively with equal volumes of water, a 5% aqueous sodium bicarbonate solution, and water. The resulting solution was concentrated to an approximately 40 wt % solution and diluted with 180 g of methyl isobutyl ketone (MIBK). Further distillation to remove residual dichloromethane, seeding with appropriate crystals, and cooling gave the product as a crystalline solid. The crystals were filtered, rinsed with 30 g of MIBK, and dried at 50° C. under reduced pressure to give 41.8 g of Compound (VIII) (89.3% yield).

Example 4—Preparation of Compound (IX)

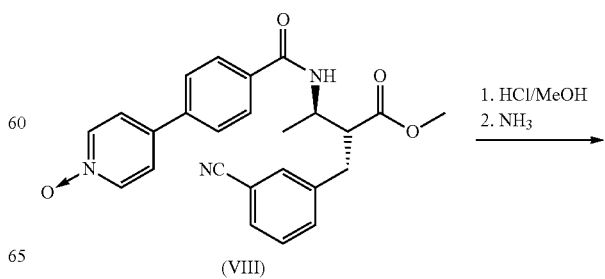

-continued

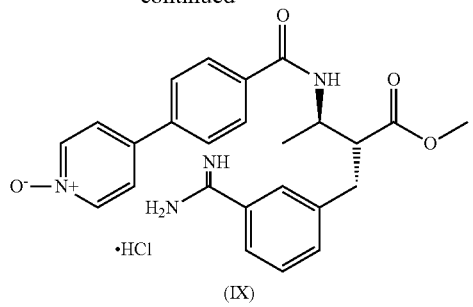

(IX)

To a 200-mL jacketed reaction flask were charged compound (VIII) (50.0 g, 116 mmol) and methanol (50 mL). This mixture was cooled to −5° C. and sealed after establishing a partial vacuum (about 100 torr). Anhydrous HCl (52.2 g, 1.43 mol) was added while maintaining the reaction temperature at less than 0° C. The reaction was stirred at 0±1° C. under closed conditions. After 16 hours, the reaction was complete (less than 2 A % (VIII) by HPLC). To the intermediate product solution was added anhydrous methanol (100 mL) while maintaining the temperature at less than 5° C. The solution was treated with $NH_3$ (27.7 g, 1.62 mol) keeping the temperature less than 0° C. Before allowing the mixture to warm to room temperature, a pH check was made of an aliquot dissolved in distilled water (a pH of 8-10 indicates a sufficient charge of ammonia). The reaction was stirred at 20° C. overnight at which point the reaction was complete.

Example 5 Manufacturing Process of Liquid Pharmaceutical Composition

The liquid pharmaceutical composition was prepared as follows:
I. Methyl (2R,3R)-2-{3-[amino(imino)methyl]benzyl}-3-{[4-(1-oxidopyridin-4-yl)benzoyl]amino}butanoate
(amounts see Table 1) was dissolved in water for injection while stirring, in a vessel made out of inert material (e.g. stainless steel or glass).
II. Sodium chloride, citric acid monohydrate, and sodium citrate (dihydrate) (amounts see Table 1) were dissolved in water for injection while stirring, in a vessel made out of inert material (e.g. stainless steel or glass) until completely dissolved. Methyl (2R,3R)-2-{3-[amino(imino)methyl]benzyl}-3-{[4-(1-oxidopyridin-4-yl)benzoyl]amino}butanoate solution from step I was added to the solution while stirring. If necessary, the pH value was adjusted using sodium hydroxide solution (e.g. 1 M sodium hydroxide) or hydrochloric acid, diluted (e.g. 1 M hydrochloric acid). Water for injection was added to adjust the final weight.
II. Filtration for Particle Load Reduction:
Solution from step II was filtered using a sterilized membrane filter (e.g. polyvinylidene difluoride, polyether sulfone or polyamide) having a nominal pore size of 0.2 μm.
IV. Solution from Step III was Filled into Sterilized, Colorless Injection Vials.
The injection vials were then closed with sterilized flip-off caps with inserted sealing discs or with injection stoppers and flanged caps with tear-off lids.
V. The sealed containers were sterilized by saturated steam in an autoclave according to Ph. Eur./USP (e.g. ≥15 minutes at ≥+121° C.).
VI. The sterilized containers were inspected for coarse contaminants, intact sealing, and particles.

Sterilization Methods for the Used Equipment
The filtration equipment (as a part of the equipment with direct product contact), the injection stoppers, and the flip-off caps with inserted sealing discs were sterilized by steam, e.g. ≥+121° C. for at least 15 minutes (Ph. Eur./USP).
The composition of the liquid pharmaceutical composition prepared is given in Table 1:

TABLE 1

| | Example | | |
|---|---|---|---|
| | A | B | C |
| Otamixaban [mg] | 1.000 | 5.000 | 50.000 |
| Citric acid monohydrate [mg] | 2.53 | 2.53 | 2.53 |
| Sodium citrate dihydrate [mg] | 3.15 | 3.15 | 3.15 |
| Sodium chloride [mg] | 7.00 | 7.00 | 7.00 |
| Water for injection | to 1.007 mL | to 1.007 mL | to 1.007 mL |

Example 6 Level of Impurities in Dependency on pH and Repeated Autoclaving

Liquid pharmaceutical compositions were prepared containing 1 mg/mL Otamixaban as described in Example 5. The appropriate pH value was adjusted by using sodium hydroxide solution (1 M sodium hydroxide) or diluted hydrochloric acid (1 M hydrochloric acid).
The content of (2R,3R)-2-(3-carbamoyl-benzyl)-3-[4-(1-oxy-pyridin-4-yl) benzoylamino]-butyric acid methyl ester and (2R,3R)-2-(3-carbamimidoyl-benzyl)-3-[4-(1-oxy-pyridin-4-yl)benzoylamino]-butyric acid was analyzed by HPLC and are shown in tables 2 and 3.

TABLE 2

Increase of (2R,3R)-2-(3-carbamoyl-benzyl)-3-[4-(1-oxy-pyridin-4-yl) benzoylamino]-butyric acid methyl ester; values were measured by HPLC and are given in %.

| | Number of autoclaving | | | |
|---|---|---|---|---|
| pH | 0 | 1 | 2 | 3 |
| 2.5 | 0.39 | 0.71 | 1.02 | 1.32 |
| 3.0 | 0.39 | 0.74 | 1.09 | 1.43 |
| 3.2 | 0.39 | 0.76 | 1.13 | 1.50 |
| 3.5 | 0.39 | 0.81 | 1.23 | 1.65 |
| 3.7 | 0.39 | 0.87 | 1.33 | 1.80 |
| 3.7 | 0.39 | 0.84 | 1.28 | 1.71 |
| 4.0 | 0.39 | 0.95 | 1.48 | 2.02 |
| 4.2 | 0.39 | 1.08 | 1.75 | 2.42 |
| 4.5 | 0.39 | 1.40 | 2.37 | 3.36 |
| 4.7 | 0.39 | 1.84 | 3.20 | 4.58 |

TABLE 3

Increase of (2R,3R)-2-(3-carbamimidoyl-benzyl)-3-[4-(1-oxy-pyridin-4-yl)benzoylamino]-butyric acid; values were measured by HPLC and are given in %.

| | Number of autoclaving | | | |
|---|---|---|---|---|
| pH | 0 | 1 | 2 | 3 |
| 2.5 | 0.10 | 0.33 | 0.56 | 0.79 |
| 3.0 | 0.08 | 0.18 | 0.26 | 0.36 |
| 3.2 | 0.08 | 0.15 | 0.21 | 0.27 |
| 3.5 | 0.08 | 0.12 | 0.17 | 0.21 |
| 3.7 | 0.08 | 0.11 | 0.16 | 0.20 |

TABLE 3-continued

Increase of (2R,3R)-2-(3-carbamimidoyl-benzyl)-3-[4-
(1-oxy-pyridin-4-yl)benzoylamino]-butyric acid; values
were measured by HPLC and are given in %.

| | Number of autoclaving | | | |
|---|---|---|---|---|
| pH | 0 | 1 | 2 | 3 |
| 3.7 | 0.08 | 0.12 | 0.16 | 0.19 |
| 4.0 | 0.08 | 0.12 | 0.16 | 0.19 |
| 4.2 | 0.07 | 0.13 | 0.18 | 0.22 |
| 4.5 | 0.08 | 0.15 | 0.24 | 0.30 |
| 4.7 | 0.08 | 0.20 | 0.32 | 0.43 |

Levels of (2R,3R)-2-(3-carbamoyl-benzyl)-3-[4-(1-oxy-pyridin-4-yl) benzoylamino]-butyric acid methyl ester were lowest at the lowest pH, whereas levels of (2R,3R)-2-(3-carbamimidoyl-benzyl)-3-[4-(1-oxy-pyridin-4-yl)benzoylamino]-butyric acid showed a minimum at pH 4.

Terminal Sterilization

The terminal sterilization was carried out in an autoclave at standard conditions of ≥15 min./≥+121° C.

The determination of Otamixaban, (2R,3R)-2-(3-carbamoyl-benzyl)-3-[4-(1-oxy-pyridin-4-yl)benzoylamino]-butyric acid methyl ester and (2R,3R)-2-(3-carbamimidoyl-benzyl)-3-[4-(1-oxy-pyridin-4-yl)benzoylamino]-butyric acid was performed by a gradient high performance liquid chromatographic system (HPLC) as follows:

Stationary phase: HP Zorbax SB-C18, 3.5 μm
Column material: stainless steel
Column length: 150 mm
Column internal diameter: 4.6 mm
Equilibration of the column: Column must be rinsed with mobile phase B (% B=25) for at least 60 minutes at a flow rate of 1 mL/min prior to sample injection.
Storage of the column: Column can be stored in acetonitrile/water=20/80 (v/v)
Mobile Phase A
Typically, 8.16 g of potassium dihydrogen phosphate anhydrous were transferred into a glass beaker. 2000 mL of water were added and adjusted to a pH of 2.15 with phosphoric acid (about 4 mL) using a pH-meter. The mobile phase was filtered through a 1.5 μm filter.
Stability of mobile phase A: 1 month at room temperature
Mobile phase B
Typically, add 500 mL of mobile phase A to 500 mL of acetonitrile. Mix and degas.
Stability of mobile phase B: 1 month at room temperature
Gradient:

| Time [min] | Mobile phase A [%] | Mobile phase B [%] |
|---|---|---|
| 0 | 75 | 25 |
| 25 | 69 | 31 |
| 45 | 20 | 80 |
| 50 | 75 | 25 |
| 60 | 75 | 25 |

The gradient may be shortened for the analysis of the standards and the system suitability tests (not for blank!) in the following way:

| Time [min] | Mobile phase A [%] | Mobile phase B [%] |
|---|---|---|
| 0 | 75 | 25 |
| 25 | 69 | 31 |

-continued

| Time [min] | Mobile phase A [%] | Mobile phase B [%] |
|---|---|---|
| 25.01 | 20 | 80 |
| 30 | 75 | 25 |
| 36 | 75 | 25 |

Procedure
Flow rate: 1 mL/min
Injection volume: 40 μl
Auto sampler temperature: Set autosampler temperature at +12° C.
Column temperature: Set oven temperature at +40° C.
Detection: 230 nm (UV)
Typical total run time: 60 min
Retention Times:
Otamixaban about 17.2 minutes
(2R,3R)-2-(3-Carbamoyl-benzyl)-3-[4-(1-oxy-pyridin-4-yl) benzoylamino]-butyric acid methyl ester about 34.9 minutes
(2R,3R)-2-(3-Carbamimidoyl-benzyl)-3-[4-(1-oxy-pyridin-4-yl)benzoylamino]-butyric acid about 7.6 minutes Example 7 Level of Impurities in Dependency on Otamixaban Concentration and Autoclaving Liquid pharmaceutical compositions were prepared containing 1, 5 or 50 mg/mL Otamixaban as described in Example 5. The appropriate pH value was adjusted by using sodium hydroxide solution (1 M sodium hydroxide) or diluted hydrochloric acid (1 M hydrochloric acid).

The content of (2R,3R)-2-(3-carbamoyl-benzyl)-3-[4-(1-oxy-pyridin-4-yl) benzoylamino]-butyric acid methyl ester was analyzed by HPLC as described in Example 6 and are shown in table 4.

TABLE 4

Increase of (2R,3R)-2-(3-carbamoyl-benzyl)-3-[4-(1-
oxy-pyridin-4-yl)benzoylamino]-butyric acid methyl
ester; values were measured by HPLC and are given in %.

| pH | Otamixaban [mg/mL] | Vial Volume [mL] | Sterilization conditions | Number of autoclaving | | | |
|---|---|---|---|---|---|---|---|
| | | | | 0 | 1 | 2 | 3 |
| 4.2 | 5 | 5 | 20 min 123° C. | 0.3 | 1.0 | 1.8 | 2.6 |
| 4.2-4.3 | 5 | 5 | 20 min 123° C. | 0.2 | 0.9 | 1.7 | 2.5 |
| 4.2 | 50 | 5 | 20 min 123° C. | 0.3 | 1.1 | 1.9 | 2.7 |
| 4.2 | 1 | 50 | 20 min 127° C. | 0.4 | 1.3 | 2.3 | n.t. |
| 4.2 | 1 | 50 | 25 min 125° C. | 0.4 | 1.3 | n.t | n.t. |
| 4.2 | 5 | 50 | 25 min 125° C. | 0.4 | 1.4 | n.t. | n.t. | n.t. means not tested

The level of (2R,3R)-2-(3-carbamoyl-benzyl)-3-[4-(1-oxy-pyridin-4-yl) benzoylamino]-butyric acid methyl ester was independent from the concentration of Otamixaban or vial volume. Additional autoclaving leads to higher levels of (2R,3R)-2-(3-carbamoyl-benzyl)-3-[4-(1-oxy-pyridin-4-yl) benzoylamino]-butyric acid methyl ester, which did not dependent on the concentration of Otamixaban or vial volume.

Example 8 Level of Impurities in Dependency on pH and Storage Time

Liquid pharmaceutical compositions were prepared containing 1 mg/mL Otamixaban as described in Example 5.

The appropriate pH value was adjusted by using sodium hydroxide solution (1 M sodium hydroxide) or diluted hydrochloric acid (1 M hydrochloric acid). The prepared vials were autoclaved one time and were stored at 40° C. and 75% RH (relative humidity).

The content of (2R,3R)-2-(3-carbamoyl-benzyl)-3-[4-(1-oxy-pyridin-4-yl) benzoylamino]-butyric acid methyl ester and (2R,3R)-2-(3-carbamimidoyl-benzyl)-3-[4-(1-oxy-pyridin-4-yl)benzoylamino]-butyric acid was analyzed by HPLC as disclosed in Example 6 and are shown in tables 5 and 6.

TABLE 5

Increase of (2R,3R)-2-(3-carbamoyl-benzyl)-3-[4-(1-oxy-pyridin-4-yl) benzoylamino]-butyric acid methyl ester; values are measured by HPLC and are given in %.

| pH | Storage time [months] | | | |
| --- | --- | --- | --- | --- |
|  | 0 | 1 | 3 | 6 |
| 2.5 | 0.71 | 0.77 | 0.86 | 0.98 |
| 3.0 | 0.74 | 0.82 | 0.96 | 1.17 |
| 3.2 | 0.76 | 0.85 | 1.00 | 1.24 |
| 3.5 | 0.81 | 0.91 | 1.06 | 1.32 |
| 3.7 | 0.87 | 0.96 | 1.15 | 1.43 |
| 4.0 | 0.95 | 1.04 | 1.23 | 1.53 |
| 4.2 | 1.08 | 1.20 | 1.39 | 1.71 |
| 4.5 | 1.40 | 1.52 | 1.76 | 2.13 |
| 4.7 | 1.84 | 1.97 | 2.24 | 2.65 |

TABLE 6

Increase of (2R,3R)-2-(3-carbamimidoyl-benzyl)-3-[4-(1-oxy-pyridin-4-yl)benzoylamino]-butyric acid; values are measured by HPLC and are given in %.

| pH | Storage time [months] | | | |
| --- | --- | --- | --- | --- |
|  | 0 | 1 | 3 | 6 |
| 2.5 | 0.33 | 1.47 | 3.73 | 7.10 |
| 3.0 | 0.18 | 0.58 | 1.39 | 2.61 |
| 3.2 | 0.15 | 0.41 | 0.93 | 1.74 |
| 3.5 | 0.12 | 0.27 | 0.55 | 0.99 |
| 3.7 | 0.11 | 0.22 | 0.42 | 0.72 |
| 4.0 | 0.12 | 0.18 | 0.32 | 0.52 |
| 4.2 | 0.13 | 0.18 | 0.27 | 0.43 |
| 4.5 | 0.15 | 0.20 | 0.30 | 0.44 |
| 4.7 | 0.20 | 0.25 | 0.36 | 0.52 |

The level of (2R,3R)-2-(3-carbamimidoyl-benzyl)-3-[4-(1-oxy-pyridin-4-yl) benzoylamino]-butyric acid increased faster with lower pH, whereas the levels of (2R,3R)-2-(3-carbamoyl-benzyl)-3-[4-(1-oxy-pyridin-4-yl)benzoylamino]-butyric acid methyl ester were parallel at different pH values, indicating the same slope and increase rate over storage time.

Example 9 Level of Impurities in Dependency on Acidic Reacting Compound and Storage Time Liquid pharmaceutical compositions were prepared containing 1 mg/mL Otamixaban basically as described in Example 5. Instead of citric acid monohydrate and sodium citrate dihydrate as used in Example 5, tartaric acid, succinic acid, malic acid and phosphoric acid were used at a level of 22.8 mMol/L. For comparison, samples without acidic reacting compound were included also. The appropriate pH value was adjusted in all samples (including also the "without" samples) by using sodium hydroxide solution (1 M sodium hydroxide) or diluted hydrochloric acid (1 M hydrochloric acid). The prepared vials were autoclaved once and were stored at 40° C. and 75% RH (relative humidity).

Terminal Sterilization

The terminal sterilization was carried out in an autoclave at standard conditions of 215 min./≥+121° C.

The determination of Otamixaban, (2R,3R)-2-(3-carbamoyl-benzyl)-3-[4-(1-oxy-pyridin-4-yl)benzoylamino]-butyric acid methyl ester and (2R,3R)-2-(3-carbamimidoyl-benzyl)-3-[4-(1-oxy-pyridin-4-yl)benzoylamino]-butyric acid was performed by a gradient high performance liquid chromatographic system (HPLC) as follows and are shown in table 7:

Stationary phase: HP Zorbax SB-C18, 3.5 µm

Column material: stainless steel

Column length: 150 mm

Column internal diameter: 4.6 mm

Equilibration of the column: Column must be rinsed with mobile phase B (% B=17) for at least 60 minutes at a flow rate of 1 mL/min prior to sample injection.

Mobile Phase A

Transfer 6.8 g of potassium dihydrogen phosphate anhydrous into a glass beaker and add 2000 mL of water. Adjust pH to 3.1 with phosphoric acid (about 0.5 mL) using a pH-meter.

Mobile Phase B

Add 200 mL of mobile phase A to 800 mL of acetonitrile, followed by mixing and degasing.

Stability of mobile phase B: 1 month at room temperature

Gradient:

| Time [min] | Mobile phase A [%] | Mobile phase B [%] |
| --- | --- | --- |
| 0 | 83 | 17 |
| 18 | 78 | 22 |
| 25 | 44 | 56 |
| 28 | 20 | 80 |
| 29 | 20 | 80 |
| 30 | 83 | 17 |
| 36 | 83 | 17 |

Procedure

Flow rate: 1 mL/min

Injection volume: 30 µl

Auto sampler temperature: Set autosampler temperature at +12° C.

Column temperature: Set oven temperature at +25° C.

Detection: 300 nm

Typical total run time: 36 min

Retention Times:

Otamixaban about 15.0 minutes (2R,3R)-2-(3-Carbamoyl-benzyl)-3-[4-(1-oxy-pyridin-4-yl) benzoylamino]-butyric acid methyl ester about 24.0 minutes (2R,3R)-2-(3-Carbamimidoyl-benzyl)-3-[4-(1-oxy-pyridin-4-yl)benzoylamino]-butyric acid about 6.9 minutes

TABLE 7

Levels of Formula II and Formula III at start and after 1 month of storage time; values are measured by HPLC and are given in %.

| Acidic reacting compound | pH Start | pH 1 month | Formula II Start | Formula II 1 month | Formula III Start | Formula III 1 month | Total impurities Start | Total impurities 1 month |
|---|---|---|---|---|---|---|---|---|
| Tartaric acid | 3.0 | 3.1 | 0.14 | 0.51 | 0.56 | 0.63 | 0.82 | 1.27 |
| Tartaric acid | 3.5 | 3.6 | 0.07 | 0.20 | 0.65 | 0.73 | 0.85 | 1.06 |
| Tartaric acid | 4.0 | 4.1 | 0.07 | 0.13 | 0.82 | 0.91 | 1.02 | 1.16 |
| Tartaric acid | 4.6 | 4.6 | 0.14 | 0.18 | 1.37 | 1.47 | 1.63 | 1.78 |
| Tartaric acid | 5.1 | 5.1 | 0.50 | 0.57 | 2.24 | 2.42 | 2.87 | 3.11 |
| Tartaric acid | 5.9 | 6.0 | 1.64 | 2.11 | 12.99 | 13.35 | 15.02 | 15.91 |
| Phosphoric acid | 3.1 | 3.1 | 0.11 | 0.42 | 0.64 | 0.71 | 0.88 | 1.26 |
| Phosphoric acid | 3.6 | 3.6 | 0.07 | 0.19 | 0.70 | 0.78 | 0.89 | 1.10 |
| Phosphoric acid | 4.2 | 4.2 | 0.08 | 0.14 | 0.91 | 1.00 | 1.11 | 1.27 |
| Phosphoric acid | 4.6 | 4.7 | 0.13 | 0.19 | 1.29 | 1.40 | 1.53 | 1.71 |
| Phosphoric acid | 5.1 | 5.1 | 0.25 | 0.34 | 2.44 | 2.56 | 2.80 | 3.03 |
| Phosphoric acid | 6.1 | 6.1 | 1.65 | 2.14 | 14.67 | 14.59 | 16.72 | 17.18 |
| Succinic acid | 3.1 | 3.1 | 0.12 | 0.43 | 0.55 | 0.63 | 0.79 | 1.19 |
| Succinic acid | 3.6 | 3.6 | 0.06 | 0.18 | 0.60 | 0.68 | 0.77 | 0.99 |
| Succinic acid | 4.0 | 4.1 | 0.06 | 0.11 | 0.77 | 0.86 | 0.95 | 1.09 |
| Succinic acid | 4.5 | 4.6 | 0.10 | 0.14 | 1.24 | 1.34 | 1.47 | 1.61 |
| Succinic acid | 5.0 | 5.1 | 0.28 | 0.35 | 2.83 | 2.94 | 3.23 | 3.42 |
| Succinic acid | 6.0 | 6.1 | 2.20 | 2.65 | 18.88 | 19.21 | 21.66 | 22.54 |
| Malic acid | 3.0 | 3.2 | 0.14 | 0.50 | 0.58 | 0.65 | 0.85 | 1.28 |
| Malic acid | 3.6 | 3.7 | 0.07 | 0.19 | 0.65 | 0.73 | 0.83 | 1.04 |
| Malic acid | 4.0 | 4.1 | 0.07 | 0.12 | 0.82 | 0.91 | 1.01 | 1.16 |
| Malic acid | 4.5 | 4.6 | 0.11 | 0.16 | 1.31 | 1.44 | 1.55 | 1.72 |
| Malic acid | 5.0 | 5.1 | 0.31 | 0.38 | 3.03 | 3.04 | 3.46 | 3.54 |
| Malic acid | 6.1 | 6.1 | 2.17 | 2.66 | 17.79 | 18.17 | 20.54 | 21.49 |
| Without | 3.2 | 3.3 | 0.09 | 0.30 | 0.52 | 0.59 | 0.73 | 1.02 |
| Without | 3.7 | 3.8 | <0.05 | 0.14 | 0.57 | 0.66 | 0.69 | 0.92 |
| Without | 4.8 | 5.5 | 0.09 | 0.23 | 1.07 | 1.36 | 1.27 | 1.72 |
| Without | 5.1 | 5.5 | 0.27 | 0.37 | 2.52 | 2.51 | 2.91 | 3.02 |
| Without | 5.6 | 5.7 | 0.28 | 0.59 | 2.45 | 2.53 | 2.86 | 3.24 |
| Without | 5.5 | 5.8 | 0.45 | 0.84 | 3.78 | 4.52 | 4.35 | 5.54 |

TABLE 8

Levels of Formula II and Formula III at start and after 2 months of storage time; values are measured by HPLC and are given in %.

| Acidic reacting compound | pH Start | pH 2 month | Formula II Start | Formula II 2 month | Formula III Start | Formula III 2 month | Total impurities Start | Total impurities 2 month |
|---|---|---|---|---|---|---|---|---|
| Tartaric acid | 3.0 | 3.0 | 0.14 | 0.97 | 0.56 | 0.73 | 0.82 | 1.82 |
| Tartaric acid | 3.5 | 3.5 | 0.07 | 0.36 | 0.65 | 0.85 | 0.85 | 1.33 |
| Tartaric acid | 4.0 | 4.0 | 0.07 | 0.20 | 0.82 | 1.06 | 1.02 | 1.37 |
| Tartaric acid | 4.6 | 4.5 | 0.14 | 0.22 | 1.37 | 1.62 | 1.63 | 1.97 |
| Tartaric acid | 5.1 | 5.0 | 0.50 | 0.69 | 2.24 | 2.91 | 2.87 | 3.73 |
| Tartaric acid | 5.9 | 6.1 | 1.64 | 2.63 | 12.99 | 13.75 | 15.02 | 16.91 |
| Phosphoric acid | 3.1 | 3.0 | 0.11 | 0.82 | 0.64 | 0.81 | 0.88 | 1.76 |
| Phosphoric acid | 3.6 | 3.6 | 0.07 | 0.33 | 0.70 | 0.89 | 0.89 | 1.35 |
| Phosphoric acid | 4.2 | 4.2 | 0.08 | 0.20 | 0.91 | 1.11 | 1.11 | 1.44 |
| Phosphoric acid | 4.6 | 4.7 | 0.13 | 0.26 | 1.29 | 1.59 | 1.53 | 1.98 |
| Phosphoric acid | 5.1 | 5.1 | 0.25 | 0.46 | 2.44 | 2.67 | 2.80 | 3.25 |
| Phosphoric acid | 6.1 | 6.1 | 1.65 | 2.84 | 14.67 | 15.58 | 16.72 | 18.99 |
| Succinic acid | 3.1 | 3.0 | 0.12 | 0.81 | 0.55 | 0.72 | 0.79 | 1.67 |
| Succinic acid | 3.6 | 3.5 | 0.06 | 0.33 | 0.60 | 0.77 | 0.77 | 1.23 |
| Succinic acid | 4.0 | 4.0 | 0.06 | 0.18 | 0.77 | 0.96 | 0.95 | 1.26 |
| Succinic acid | 4.5 | 4.5 | 0.10 | 0.19 | 1.24 | 1.47 | 1.47 | 1.79 |
| Succinic acid | 5.0 | 5.0 | 0.28 | 0.45 | 2.83 | 3.16 | 3.23 | 3.74 |
| Succinic acid | 6.0 | 6.1 | 2.20 | 3.20 | 18.88 | 19.53 | 21.66 | 23.52 |
| Malic acid | 3.0 | 3.0 | 0.14 | 0.93 | 0.58 | 0.72 | 0.85 | 1.78 |
| Malic acid | 3.6 | 3.5 | 0.07 | 0.33 | 0.65 | 0.82 | 0.83 | 1.28 |
| Malic acid | 4.0 | 4.0 | 0.07 | 0.19 | 0.82 | 1.03 | 1.01 | 1.34 |
| Malic acid | 4.5 | 4.5 | 0.11 | 0.21 | 1.31 | 1.58 | 1.55 | 1.97 |
| Malic acid | 5.0 | 5.0 | 0.31 | 0.47 | 3.03 | 3.24 | 3.46 | 3.83 |

TABLE 8-continued

Levels of Formula II and Formula III at start and after 2 months of storage time; values are measured by HPLC and are given in %.

| Acidic reacting compound | pH Start | pH 2 month | Formula II Start | Formula II 2 month | Formula III Start | Formula III 2 month | Total impurities Start | Total impurities 2 month |
|---|---|---|---|---|---|---|---|---|
| Malic acid | 6.1 | 6.1 | 2.17 | 3.31 | 17.79 | 18.73 | 20.54 | 22.82 |
| Without | 3.2 | 3.2 | 0.09 | 0.56 | 0.52 | 0.67 | 0.73 | 1.36 |
| Without | 3.7 | 3.8 | <0.05 | 0.28 | 0.57 | 0.77 | 0.69 | 1.18 |
| Without | 5.1 | 5.4 | 0.27 | 0.69 | 2.52 | 2.97 | 2.91 | 3.79 |
| Without | 4.8 | 5.8 | 0.09 | 0.62 | 1.07 | 1.76 | 1.27 | 2.50 |
| Without | 5.6 | 5.9 | 0.28 | 0.71 | 2.45 | 2.62 | 2.86 | 3.46 |
| Without | 5.5 | 6.0 | 0.45 | 1.05 | 3.78 | 4.24 | 4.35 | 5.52 |

TABLE 9

Levels of Formula II and Formula III at start and after 3 months of storage time; values are measured by HPLC and are given in %.

| Acidic reacting compound | pH Start | pH 3 month | Formula II Start | Formula II 2 month | Formula III Start | Formula III 3 month | Total impurities Start | Total impurities 3 month |
|---|---|---|---|---|---|---|---|---|
| Tartaric acid | 3.0 | 3.0 | 0.14 | 1.37 | 0.56 | 0.81 | 0.82 | 2.30 |
| Tartaric acid | 3.5 | 3.5 | 0.07 | 0.50 | 0.65 | 0.94 | 0.85 | 1.56 |
| Tartaric acid | 4.0 | 4.0 | 0.07 | 0.26 | 0.82 | 1.20 | 1.02 | 1.63 |
| Tartaric acid | 4.6 | 4.6 | 0.14 | 0.27 | 1.37 | 1.76 | 1.63 | 2.15 |
| Tartaric acid | 5.1 | 5.1 | 0.50 | 0.78 | 2.24 | 3.06 | 2.87 | 3.95 |
| Tartaric acid | 5.9 | 6.0 | 1.64 | 3.24 | 12.99 | 14.16 | 15.02 | 18.01 |
| Phosphoric acid | 3.1 | 3.1 | 0.11 | 1.17 | 0.64 | 0.89 | 0.88 | 2.24 |
| Phosphoric acid | 3.6 | 3.6 | 0.07 | 0.46 | 0.70 | 0.99 | 0.89 | 1.57 |
| Phosphoric acid | 4.2 | 4.2 | 0.08 | 0.26 | 0.91 | 1.21 | 1.11 | 1.59 |
| Phosphoric acid | 4.6 | 4.7 | 0.13 | 0.34 | 1.29 | 1.69 | 1.53 | 2.20 |
| Phosphoric acid | 5.1 | 5.1 | 0.25 | 0.58 | 2.44 | 2.91 | 2.80 | 3.61 |
| Phosphoric acid | 6.1 | 6.0 | 1.65 | 3.44 | 14.67 | 16.22 | 16.72 | 20.33 |
| Succinic acid | 3.1 | 3.1 | 0.12 | 1.16 | 0.55 | 0.80 | 0.79 | 2.09 |
| Succinic acid | 3.6 | 3.5 | 0.06 | 0.46 | 0.60 | 0.86 | 0.77 | 1.44 |
| Succinic acid | 4.0 | 4.0 | 0.06 | 0.23 | 0.77 | 1.07 | 0.95 | 1.42 |
| Succinic acid | 4.5 | 4.5 | 0.10 | 0.24 | 1.24 | 1.62 | 1.47 | 1.98 |
| Succinic acid | 5.0 | 5.0 | 0.28 | 0.54 | 2.83 | 3.31 | 3.23 | 3.97 |
| Succinic acid | 6.0 | 6.0 | 2.20 | 3.70 | 18.88 | 19.85 | 21.66 | 24.44 |
| Malic acid | 3.0 | 3.0 | 0.14 | 1.33 | 0.58 | 0.80 | 0.85 | 2.32 |
| Malic acid | 3.6 | 3.6 | 0.07 | 0.47 | 0.65 | 0.92 | 0.83 | 1.51 |
| Malic acid | 4.0 | 4.0 | 0.07 | 0.24 | 0.82 | 1.12 | 1.01 | 1.49 |
| Malic acid | 4.5 | 4.5 | 0.11 | 0.25 | 1.31 | 1.70 | 1.55 | 2.08 |
| Malic acid | 5.0 | 5.1 | 0.31 | 0.56 | 3.03 | 3.49 | 3.46 | 4.18 |
| Malic acid | 6.1 | 6.1 | 2.17 | 3.84 | 17.79 | 18.77 | 20.54 | 23.48 |
| Without | 3.2 | 3.2 | 0.09 | 0.80 | 0.52 | 0.76 | 0.73 | 1.69 |
| Without | 3.7 | 3.8 | <0.05 | 0.32 | 0.57 | 0.83 | 0.69 | 1.28 |
| Without | 5.1 | 5.8 | 0.27 | 0.94 | 2.52 | 2.92 | 2.91 | 3.98 |
| Without | 4.8 | 5.7 | 0.09 | 0.50 | 1.07 | 1.66 | 1.27 | 2.29 |
| Without | 5.6 | 5.8 | 0.28 | 1.26 | 2.45 | 3.12 | 2.86 | 4.50 |
| Without | 5.5 | 6.1 | 0.45 | 2.18 | 3.78 | 5.40 | 4.35 | 7.85 |

The level of (2R,3R)-2-(3-carbamimidoyl-benzyl)-3-[4-(1-oxy-pyridin-4-yl) benzoylamino]-butyric acid increased faster with lower/higher pH, whereas the levels of (2R,3R)-2-(3-carbamoyl-benzyl)-3-[4-(1-oxy-pyridin-4-yl)benzoylamino]-butyric acid methyl ester were parallel at different pH values, indicating the same slope and increase rate over storage time. Both trends were independent on the used acidic reacting compound.

Example 10 Level of Impurities in Dependency on Citric Acid and Storage Time

Liquid pharmaceutical compositions were prepared containing 1 mg/mL Otamixaban as described in Example 9. Citric acid was used at a level of 22.8 mmol/L. The appropriate pH value was adjusted by using sodium hydroxide solution (1 M sodium hydroxide) or diluted hydrochloric acid (1 M hydrochloric acid). The prepared vials were autoclaved once and were stored at 40° C. and 75% RH (relative humidity).

The content of (2R,3R)-2-(3-carbamimidoyl-benzyl)-3-[4-(1-oxy-pyridin-4-yl) benzoylamino]-butyric acid (Formula II) and (2R,3R)-2-(3-carbamoyl-benzyl)-3-[4-(1-oxy-pyridin-4-yl)benzoylamino]-butyric acid methyl ester (Formula III) was analyzed by HPLC as disclosed in Example 9 and are shown in table 9.

TABLE 10

Levels of Formula II and Formula III at start and after 1 month of storage time; values are measured by HPLC and are given in %.

|  | pH Start | pH 1 month | Formula II Start | Formula II 1 month | Formula III Start | Formula III 1 month | Total impurities Start | Total impurities 1 month |
|---|---|---|---|---|---|---|---|---|
| Citric acid | 3.0 | 3.1 | 0.15 | 0.55 | 0.58 | 0.65 | 0.87 | 1.33 |
|  | 3.6 | 3.6 | 0.08 | 0.22 | 0.62 | 0.70 | 0.83 | 1.06 |
|  | 4.0 | 4.1 | 0.06 | 0.13 | 0.77 | 0.91 | 0.98 | 1.17 |
|  | 4.6 | 4.6 | 0.11 | 0.15 | 1.25 | 1.39 | 1.51 | 1.75 |
|  | 5.1 | 5.1 | 0.32 | 0.40 | 3.12 | 3.28 | 3.57 | 3.80 |
|  | 6.1 | 6.1 | 2.78 | 3.25 | 23.43 | 23.87 | 27.12 | 28.16 |

TABLE 11

Levels of Formula II and Formula III at start and after 2 months of storage time; values are measured by HPLC and are given in %.

|  | pH Start | pH 2 month | Formula II Start | Formula II 2 month | Formula III Start | Formula III 2 month | Total impurities Start | Total impurities 2 month |
|---|---|---|---|---|---|---|---|---|
| Citric acid | 3.0 | 3.0 | 0.15 | 1.03 | 0.58 | 0.75 | 0.87 | 1.92 |
|  | 3.6 | 3.5 | 0.08 | 0.39 | 0.62 | 0.80 | 0.83 | 1.33 |
|  | 4.0 | 4.0 | 0.06 | 0.21 | 0.77 | 1.06 | 0.98 | 1.40 |
|  | 4.6 | 4.5 | 0.11 | 0.20 | 1.25 | 1.53 | 1.51 | 1.94 |
|  | 5.1 | 5.1 | 0.32 | 0.49 | 3.12 | 3.45 | 3.57 | 4.08 |
|  | 6.1 | 6.1 | 2.78 | 3.82 | 23.43 | 24.36 | 27.12 | 29.39 |

TABLE 12

Levels of Formula II and Formula III at start and after 3 months of storage time; values are measured by HPLC and are given in %.

|  | pH Start | pH 3 month | Formula II Start | Formula II 3 month | Formula III Start | Formula III 3 month | Total impurities Start | Total impurities 3 month |
|---|---|---|---|---|---|---|---|---|
| Citric acid | 3.0 | 3.0 | 0.15 | 1.48 | 0.58 | 0.82 | 0.87 | 2.43 |
|  | 3.6 | 3.5 | 0.08 | 0.55 | 0.62 | 0.90 | 0.83 | 1.58 |
|  | 4.0 | 4.0 | 0.06 | 0.27 | 0.77 | 1.12 | 0.98 | 1.53 |
|  | 4.6 | 4.5 | 0.11 | 0.26 | 1.25 | 1.68 | 1.51 | 2.13 |
|  | 5.1 | 5.1 | 0.32 | 0.59 | 3.12 | 3.69 | 3.57 | 4.41 |
|  | 6.1 | 6.1 | 2.78 | 4.37 | 23.43 | 24.52 | 27.12 | 30.23 |

Example 11 Level of Impurities in Dependency on Acidic Reacting Compound, pH and Repeated Autoclaving Liquid pharmaceutical compositions were prepared containing 1 mg/mL Otamixaban basically as described in Example 5. Instead of citric acid monohydrate and sodium citrate dihydrate as used in Example 5, tartaric acid, succinic acid, malic acid, citric acid and phosphoric acid were used at a level of 22.8 mMol/L. For comparison, samples without acidic reacting compound were included also. The appropriate pH value was adjusted by using sodium hydroxide solution (1 M sodium hydroxide) or diluted hydrochloric acid (1 M hydrochloric acid). The prepared vials were autoclaved once and twice by terminal sterilization. The terminal sterilization was carried out in an autoclave at standard conditions of ≥15 min./≥+121° C.

The content of (2R,3R)-2-(3-carbamimidoyl-benzyl)-3-[4-(1-oxy-pyridin-4-yl) benzoylamino]-butyric acid (Formula II) and (2R,3R)-2-(3-carbamoyl-benzyl)-3-[4-(1-oxy-pyridin-4-yl)benzoylamino]-butyric acid methyl ester (Formula III) was analyzed by HPLC as disclosed in Example 9 and are shown in tables 10 and 11.

TABLE 13

Levels of Formula II at start and after 1 or 2 times of autoclaving; values are measured by HPLC and are given in %.

| Acidic reacting compound | pH/No. of autoclaving Start | pH/No. of autoclaving 1 | pH/No. of autoclaving 2 | Formula II/Number of autoclaving Start | Formula II/Number of autoclaving 1 | Formula II/Number of autoclaving 2 |
|---|---|---|---|---|---|---|
| Tartaric acid | 3.1 | 3.0 | 3.1 | <0.05 | 0.14 | 0.24 |
| Tartaric acid | 3.6 | 3.5 | 3.5 | <0.05 | 0.07 | 0.12 |
| Tartaric acid | 4.1 | 4.0 | 4.0 | <0.05 | 0.07 | 0.13 |
| Tartaric acid | 4.6 | 4.6 | 4.6 | <0.05 | 0.14 | 0.24 |
| Tartaric acid | 5.1 | 5.1 | 5.0 | 0.29 * | 0.50 | 0.79 |
| Tartaric acid | 6.0 | 5.9 | 5.9 | <0.05 | 1.64 | 2.94 |
| Phosphoric acid | 3.1 | 3.1 | 3.1 | <0.05 | 0.11 | 0.19 |
| Phosphoric acid | 3.7 | 3.6 | 3.6 | <0.05 | 0.07 | 0.12 |
| Phosphoric acid | 4.2 | 4.2 | 4.2 | <0.05 | 0.08 | 0.14 |
| Phosphoric acid | 4.7 | 4.6 | 4.7 | <0.05 | 0.13 | 0.24 |
| Phosphoric acid | 5.1 | 5.1 | 5.1 | <0.05 | 0.25 | 0.47 |
| Phosphoric acid | 6.1 | 6.1 | 6.0 | <0.05 | 1.65 | 2.95 |
| Succinic acid | 3.2 | 3.1 | 3.1 | <0.05 | 0.12 | 0.22 |
| Succinic acid | 3.7 | 3.6 | 3.6 | <0.05 | 0.06 | 0.11 |
| Succinic acid | 4.1 | 4.0 | 4.1 | <0.05 | 0.06 | 0.10 |
| Succinic acid | 4.6 | 4.5 | 4.5 | <0.05 | 0.10 | 0.18 |
| Succinic acid | 5.1 | 5.0 | 5.1 | <0.05 | 0.28 | 0.55 |

TABLE 13-continued

Levels of Formula II at start and after 1 or 2 times of autoclaving; values are measured by HPLC and are given in %.

| Acidic reacting compound | pH/No. of autoclaving | | | Formula II/Number of autoclaving | | |
|---|---|---|---|---|---|---|
| | Start | 1 | 2 | Start | 1 | 2 |
| Succinic acid | 6.0 | 6.0 | 6.0 | <0.05 | 2.20 | 3.79 |
| Malic acid | 3.1 | 3.0 | 3.1 | <0.05 | 0.14 | 0.24 |
| Malic acid | 3.6 | 3.6 | 3.6 | <0.05 | 0.07 | 0.12 |
| Malic acid | 4.1 | 4.0 | 4.1 | <0.05 | 0.07 | 0.11 |
| Malic acid | 4.6 | 4.5 | 4.6 | <0.05 | 0.11 | 0.22 |
| Malic acid | 5.1 | 5.0 | 5.1 | <0.05 | 0.31 | 0.60 |
| Malic acid | 6.1 | 6.1 | 6.0 | <0.05 | 2.17 | 3.81 |
| Citric acid | 3.0 | 3.0 | 3.1 | <0.05 | 0.15 | 0.28 |
| Citric acid | 3.6 | 3.6 | 3.6 | <0.05 | 0.08 | 0.13 |
| Citric acid | 4.0 | 4.0 | 4.1 | <0.05 | 0.06 | 0.11 |
| Citric acid | 4.6 | 4.6 | 4.6 | <0.05 | 0.11 | 0.19 |
| Citric acid | 5.1 | 5.1 | 5.1 | <0.05 | 0.32 | 0.60 |
| Citric acid | 6.1 | 6.1 | 6.1 | <0.05 | 2.78 | 4.64 |
| Without | 3.2 | 3.2 | 3.3 | <0.05 | 0.09 | 0.12 |
| Without | 3.7 | 3.7 | 3.8 | <0.05 | <0.05 | 0.09 |
| Without | 5.1 | 5.1 | 6.4 | <0.05 | 0.27 | 0.53 |
| Without | 4.8 | 4.8 | 5.6 | <0.05 | 0.09 | 0.18 |
| Without | 5.6 | 5.6 | 5.9 | <0.05 | 0.28 | 0.60 |
| Without | 5.5 | 5.5 | 5.7 | <0.05 | 0.45 | 0.96 |

<means less than
* outlying data

TABLE 14

Levels of Formula III at start and after 1 or 2 times of autoclaving; values are measured by HPLC and are given in %.

| Acidic reacting compound | pH/No. of autoclaving | | | Formula III/Number of autoclaving | | |
|---|---|---|---|---|---|---|
| | Start | 1 | 2 | Start | 1 | 2 |
| Tartaric acid | 3.1 | 3.0 | 3.1 | 0.20 | 0.56 | 0.96 |
| Tartaric acid | 3.6 | 3.5 | 3.5 | 0.20 | 0.65 | 1.14 |
| Tartaric acid | 4.1 | 4.0 | 4.0 | 0.20 | 0.82 | 1.56 |
| Tartaric acid | 4.6 | 4.6 | 4.6 | 0.21 | 1.37 | 2.60 |
| Tartaric acid | 5.1 | 5.1 | 5.0 | 0.27 | 2.24 | 5.09 |
| Tartaric acid | 6.0 | 5.9 | 5.9 | 0.21 | 12.99 | 23.93 |
| Phosphoric acid | 3.1 | 3.1 | 3.1 | 0.20 | 0.64 | 1.10 |
| Phosphoric acid | 3.7 | 3.6 | 3.6 | 0.20 | 0.70 | 1.26 |
| Phosphoric acid | 4.2 | 4.2 | 4.2 | 0.20 | 0.91 | 1.69 |
| Phosphoric acid | 4.7 | 4.6 | 4.7 | 0.20 | 1.29 | 2.60 |
| Phosphoric acid | 5.1 | 5.1 | 5.1 | 0.20 | 2.44 | 4.69 |
| Phosphoric acid | 6.1 | 6.1 | 6.0 | 0.21 | 14.67 | 26.71 |
| Succinic acid | 3.2 | 3.1 | 3.1 | 0.20 | 0.55 | 0.94 |
| Succinic acid | 3.7 | 3.6 | 3.6 | 0.20 | 0.60 | 1.04 |
| Succinic acid | 4.1 | 4.0 | 4.1 | 0.20 | 0.77 | 1.38 |
| Succinic acid | 4.6 | 4.5 | 4.5 | 0.21 | 1.24 | 2.32 |
| Succinic acid | 5.1 | 5.0 | 5.1 | 0.21 | 2.83 | 5.55 |
| Succinic acid | 6.0 | 6.0 | 6.0 | 0.21 | 18.88 | 32.58 |
| Malic acid | 3.1 | 3.0 | 3.1 | 0.20 | 0.58 | 0.94 |
| Malic acid | 3.6 | 3.6 | 3.6 | 0.20 | 0.65 | 1.10 |
| Malic acid | 4.1 | 4.0 | 4.1 | 0.20 | 0.82 | 1.43 |
| Malic acid | 4.6 | 4.5 | 4.6 | 0.21 | 1.31 | 2.55 |
| Malic acid | 5.1 | 5.0 | 5.1 | 0.21 | 3.03 | 5.84 |
| Malic acid | 6.1 | 6.1 | 6.0 | 0.21 | 17.79 | 31.62 |
| Citric acid | 3.0 | 3.0 | 3.1 | 0.20 | 0.58 | 0.97 |
| Citric acid | 3.6 | 3.6 | 3.6 | 0.20 | 0.62 | 1.07 |
| Citric acid | 4.0 | 4.0 | 4.1 | 0.20 | 0.77 | 1.41 |
| Citric acid | 4.6 | 4.6 | 4.6 | 0.20 | 1.25 | 2.41 |
| Citric acid | 5.1 | 5.1 | 5.1 | 0.21 | 3.12 | 6.01 |
| Citric acid | 6.1 | 6.1 | 6.1 | 0.21 | 23.43 | 38.79 |
| Without | 3.2 | 3.2 | 3.3 | 0.20 | 0.52 | 0.94 |
| Without | 3.7 | 3.7 | 3.8 | 0.20 | 0.57 | 0.98 |
| Without | 4.8 | 4.8 | 5.6 | 0.21 | 1.07 | 2.03 |
| Without | 5.5 | 5.5 | 5.7 | 0.21 | 3.78 | 8.08 |
| Without | 5.6 | 5.6 | 5.9 | 0.21 | 2.45 | 5.21 |
| Without | 5.1 | 5.1 | 6.4 | 0.20 | 2.52 | 4.77 |

The levels for Formula III are higher than for Formula II and increase in a about linear dependency from the number of autoclaving. The levels of impurity for Formula II and Formula III depend on the pH of the tested liquid pharmaceutical composition and are independent on the used acidic reacting compound.

The invention claimed is:

1. A method of minimizing impurities in an aqueous pharmaceutical composition for injection comprising methyl (2R,3R)-2-{3-[amino(imino)methyl]benzyl}-3-{[4-(1-oxidopyridin-4-yl)benzoyl]amino}butanoate, the method comprising the steps of:
    a) dissolving methyl (2R,3R)-2-{3-[amino(imino)methyl]benzyl}-3-{[4-(1-oxidopyridin-4-yl)benzoyl]amino}butanoate in water to form a first aqueous solution;
    b) dissolving an acidic reacting compound, a salt thereof, or a mixture of the foregoing, in water to form a second aqueous solution;
    c) adding the first aqueous solution from step a) to the second aqueous solution from step b) to form a third aqueous solution; and
    d) adjusting the pH of the third aqueous solution from step c) to a pH from about 3 to about 5.0 to form the aqueous pharmaceutical composition,
wherein the aqueous pharmaceutical composition comprises from 0.1 mg/mL to 60 mg/mL of methyl (2R,3R)-2-{3-[amino(imino)methyl]benzyl}-3-{[4-(1-oxidopyridin-4-yl)benzoyl]amino}butanoate, and from 1 mMol/L to 1000 mMol/L of the acidic reacting compound, a salt thereof, or a mixture of the foregoing; and
wherein the aqueous pharmaceutical composition contains (i) a maximum impurity level of (2R,3R)-2-(3-Carbamimidoyl-benzyl)-3-[4-(1-oxy-pyridin-4-yl)benzoylamino]-butyric acid that does not exceed about 8.0% after storage for 1-6 months at 40° C. and 75% relative humidity, and (ii) a maximum impurity level of (2R,3R)-2-(3-Carbamoyl-benzyl)-3-[4-(1-oxy-pyridin-4-yl) benzoylamino]-butyric acid methyl ester that does not exceed about 5.0% after storage for 1-6 months at 40° C. and 75% relative humidity.

2. The method of claim 1, wherein the acidic reacting compound is selected from the group consisting of citric acid, acetic acid, glycolic acid, lactic acid, pyruvic acid, malonic acid, succinic acid, glutaric acid, fumaric acid, malic acid, tartaric acid, ascorbic acid, maleic acid, hydroxymaleic acid, benzoic acid, hydroxybenzoic acid, phenylacetic acid, cinnamic acid, salicyclic acid, 2-phenoxybenzoic acid, p-toluenesulfonic acid, methanesulfonic acid, 2-hydroxyethanesulfonic acid, hyaluronic acid, and acetyl salicylic acid, or is an amino acid, or is a mineral acid selected from the group consisting of hydrochloric acid and phosphoric acid, or is a salt of said organic acid, amino acid, or mineral acid, or is a mixture of any of the foregoing.

3. The method of claim 2, wherein the acidic reacting compound is selected from the group consisting of citric acid and sodium citrate, or is a mixture thereof.

4. The method of claim 1, wherein the aqueous pharmaceutical composition comprises from 1.0 mg/mL to 50 mg/mL of methyl (2R,3R)-2-{3-[amino(imino) methyl]benzyl}-3-{[4-(1-oxidopyridin-4-yl)benzoyl]amino}butanoate, and from 20 mMol/L to 25 mMol/L of the acidic reacting compound, a salt thereof, or a mixture of the foregoing.

5. The method of claim 4, wherein the aqueous pharmaceutical composition comprises from 1.0 mg/mL to 5 mg/mL methyl of (2R,3R)-2-{3-[amino(imino)methyl]benzyl}-3-{[4-(1-oxidopyridin-4-yl)benzoyl]amino}butanoate, and from 20 mMol/L to 25 mMol/L of the acidic reacting compound, a salt thereof, or a mixture of the foregoing.

6. The method of claim 1, wherein the pH of the third aqueous solution from step c) is adjusted to a pH from about 3 to about 4.7.

7. The method of claim 6, wherein the pH of the third aqueous solution from step c) is adjusted to a pH from about 3.7 to about 4.3.

8. The method of claim 6, wherein the pH of the third aqueous solution from step c) is adjusted to a pH from 4.0 to about 4.2.

9. The method of claim 1, wherein the maximum impurity level of (2R,3R)-2-(3-Carbamimidoyl-benzyl)-3-[4-(1-oxy-pyridin-4-yl)benzoylamino]-butyric acid is from 0.3% to 4.0%.

10. The method of claim 1, wherein the maximum impurity level of (2R,3R)-2-(3-Carbamimidoyl-benzyl)-3-[4-(1-oxy-pyridin-4-yl)benzoylamino]-butyric acid is from 0.4% to 1.8%.

11. The method of claim 1, wherein the maximum impurity level of (2R,3R)-2-(3-Carbamoyl-benzyl)-3-[4-(1-oxy-pyridin-4-yl)benzoylamino]-butyric acid methyl ester is from 0.7% to 4.5%.

12. The method of claim 1, wherein the maximum impurity level of (2R,3R)-2-(3-Carbamoyl-benzyl)-3-[4-(1-oxy-pyridin-4-yl)benzoylamino]-butyric acid methyl ester is from 0.9% to 3.5%.

13. The method of claim 1, wherein the aqueous pharmaceutical composition is sterile.

\* \* \* \* \*